(12) United States Patent
Seeley

(10) Patent No.: US 7,247,189 B2
(45) Date of Patent: Jul. 24, 2007

(54) DEVICE FOR COMBINING TWO FLUID STREAMS

(75) Inventor: John V. Seeley, Grand Blanc, MI (US)

(73) Assignee: Oakland University, Rochester, MI (US)

( * ) Notice: Subject to any disclaimer, the term of this patent is extended or adjusted under 35 U.S.C. 154(b) by 334 days.

(21) Appl. No.: 10/840,767

(22) Filed: May 6, 2004

(65) Prior Publication Data

US 2004/0232366 A1    Nov. 25, 2004

Related U.S. Application Data

(60) Provisional application No. 60/471,640, filed on May 19, 2003.

(51) Int. Cl.
*B01D 53/02* (2006.01)
(52) U.S. Cl. .................... 95/82; 95/89; 96/102; 96/105
(58) Field of Classification Search .................. 95/82, 95/89; 96/101, 102, 105; 73/23.42
See application file for complete search history.

(56) References Cited

U.S. PATENT DOCUMENTS 5,391,221 A * 2/1995 Fukushima et al. ............ 95/82
6,632,268 B2   10/2003 Seeley

OTHER PUBLICATIONS

Liu, Z.Y., et al., J. Chromatogr. Sci. 29 227 (1991).
Kinghorn, R.M., et al., Hrc-J High Res Chrom 23 245 (2000).
Ledford, E.B., et al., Hrc-J High Res Chrom 23 202 (2000).
Beens, J., et al., J Chromatogr A 919 127 (2001).
Adahchour, M., et al., Analyst 128 213 (2003).
Bruckner, C.A., et al., Anal Chem 70 2796 (1998).
Seeley, J.V., et al., Anal Chem 72 4346 (2000).
Seeley, J.V., J Chromatogr A 962 21 (2002).
Bushey, M.M., et al., Anal Chem 62 161 (1990).
Seeley, J.V., et al., J Sep Sci 24 444 (2001).
Gaspar, G., et al., Anal Chem 50 1512 (1978).
Sinha, A.E., et al., J Chromatogr A 983 195 (2003).
Deans, D.R., Chromatographia 1 18 (1968).
Sacks, R., et al., Environmental Science and Technology 28 428A (1994).
Giddings, J.C., Unified Separation Science, Wiley, New York (1991).
Gaines, R.B., et al., Environmental Science and Technology 33 2106 (1999).
Bueno, P.A.B., et al., J. Chromatogr. 1027, 3-10 (A 2004).
Murphy, R.E., et al., Anal. Chem. 70 1585-1594 (1998).
Kinghorn, R.M., et al., J. High Resol. Chromatogr. 21 620-622 (1998).

* cited by examiner

*Primary Examiner*—Robert Hopkins
(74) *Attorney, Agent, or Firm*—Ian C. McLeod; Steven E. Merritt

(57) ABSTRACT

A fluidic switching device is particularly for use in chromatography is described. The device allows a rapid switching between chromatographic columns; particularly, in gas chromatography.

15 Claims, 21 Drawing Sheets

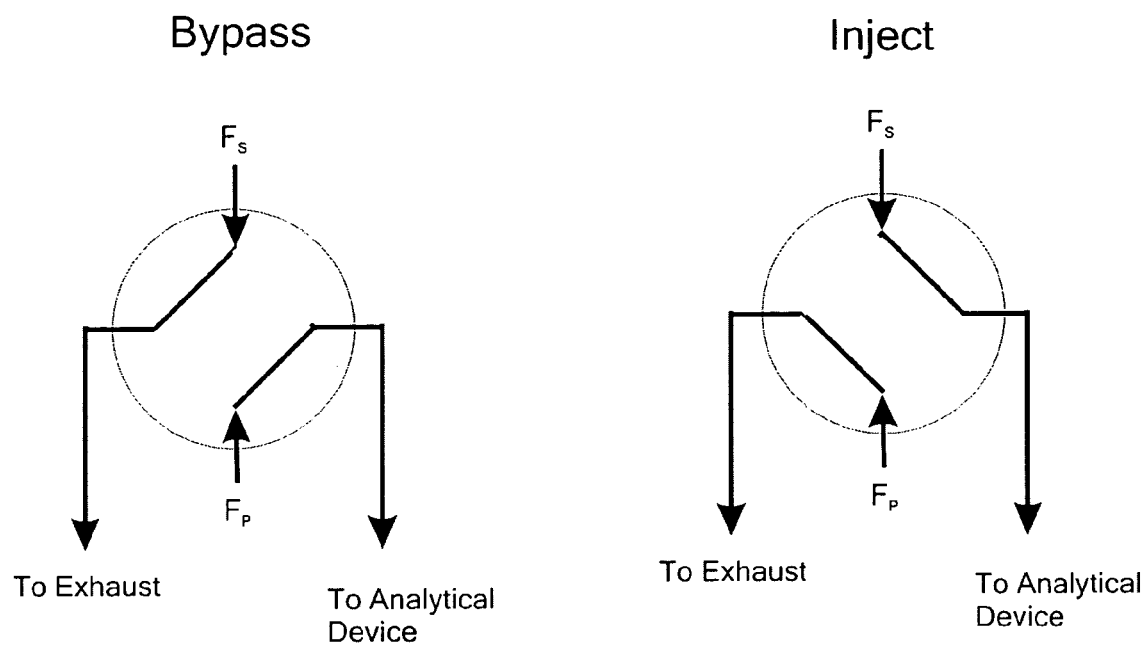
FIGURE 1A  Secondary Column        FIGURE 1B  Secondary Column
PRIOR ART

Bypass

To Exhaust    To Analytical Device

Inject

To Exhaust    To Analytical Device

Load                                               Inject
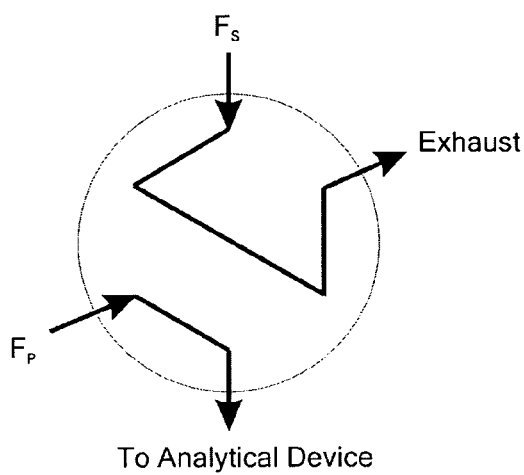 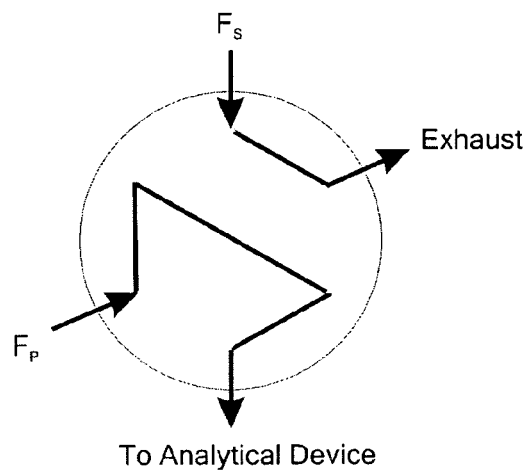
FIGURE 3A                             FIGURE 3B
PRIOR ART Load Left / Inject Right To Analytical Device Load Right / Inject Left To Analytical Device

DEVICE FOR COMBINING TWO FLUID STREAMS

CROSS-REFERENCE TO RELATED APPLICATION

This application claims priority to provisional application Ser. No. 60/471,640, filed May 19, 2003.

GOVERNMENT RIGHTS

The invention disclosed in this application was supported by the National Science Foundation Project No. 0094185. The Government has certain rights to this invention.

BACKGROUND OF THE INVENTION

The present invention relates to a fluidic switching device particularly for use in chromatography. The device is particularly useful in gas chromatography for switching between first and second columns. In particular, the device can be used in place of the high speed diaphragm valve in two dimensional gas chromatography as described in my U.S. patent application Ser. No. 10/067,378, filed Feb. 4, 2002, now U.S. Pat. No. 6,632,268, which is incorporated by reference in its entirety herein.

DESCRIPTION OF RELATED ART

John B. Phillips and Zaiyou Liu introduced comprehensive two-dimensional gas chromatography (GC×GC) twelve years ago (Liu, Z. Y., et al., J. Chromatogr. Sci. 29 227 (1991)). Their original design employed a two-stage thermal modulator. This modulator was effective at demonstrating the resolving power of GC×GC separations but not sufficiently robust for routine use. Several new modulators have been introduced over the past decade. Current thermal modulators employ cryogenic sampling (Kinghorn, R. M., et al., Hrc-J High Res Chrom 23 245 (2000); Ledford, E. B., et al., Hrc-J High Res Chrom 23 202 (2000); Beens, J., et al., J Chromatogr A 919 127 (20010); and Adahchour, M., et al., Analyst 128 213 (20003)). These devices are applicable to a broad range of samples and are much more rugged than the original design. The main disadvantages are that liquid cryogen is required and a system capable of delivering liquid cryogen into the oven of the gas chromatograph must be engineered.

A few investigators have developed modulation schemes that do not employ thermal techniques. Current designs use multi-port valves to either divert a portion of the primary column effluent to the head of the secondary column (Bruckner, C. A., et al., Anal Chem 70 2796 (1998)) or to collect primary column effluent in a sampling loop and subsequently inject the material into the secondary column (Seeley, J. V., et al., Anal Chem 72 4346 (2000)). The direct diverting approach reduces the sensitivity of the analysis because only a small amount (<10%) of each component is transferred from the primary column to the secondary column. The low duty cycle of sampling can also lead to imprecision in component quantitation (Seeley, J. V., J Chromatogr A 962 21 (2002)).

A multi-port, two-position valve fitted with a sample loop can provide greater component transfer and reduce quantitative imprecision (Seeley, J. V., et al., Anal Chem 72 4346 (2000)). Similar devices have been fabricated with 8-port valves (Bushey, M. M., et al., Anal Chem 62 161 (1990)). When the valve is in the "fill" position, primary column effluent flows into the sample loop while an auxiliary flow of carrier gas is directed to the secondary column. When the valve is switched to the "flush" position, primary column effluent is directed to the exhaust while the auxiliary flow flushes the sample loop contents into the secondary column. After the loop is flushed, the valve is returned to the "fill" position to begin collecting more primary column effluent. If the volumetric flow rate of the primary column and the secondary column are equal, then the time required to flush the loop is the same as the time required to fill the loop. However, if the secondary column flow is greater than the primary column flow then the loop will be flushed in less time than it was filled. In practice, a primary to secondary flow ratio of 1:20 is often used (Seeley, J. V., et al., J Sep Sci 24 444 (2001)). Under such conditions, the entire volume of primary column effluent collected in 1.0 s can be injected into the secondary column as a 50 ms wide pulse. This approach is called differential flow modulation.

There are three drawbacks to the differential flow modulation approach. First, high secondary flows are required to produce high peak capacity. High flows lead to an increase in the theoretical plate height of the secondary column, but high flows also allow longer secondary columns to be used. As a result, the total number of accessible theoretical plates is largely independent of flow (Gaspar, G., et al., Anal Chem 50 1512 (1978)). However, the requirement of high flow and long columns limits the use of micro-bore secondary columns (i.e., columns with internal diameters less than 0.15 mm) because excessively high head pressures would be required.

Temperature limitations are a second drawback of differential flow modulation. Diaphragm valves are currently the only multi-port valves capable of continuous switching at a rate of 1 Hz. Such valves have internal actuating mechanisms that are damaged at temperatures greater than 200° C. This reduces the range of samples that can be analyzed. For example, diesel fuel contains semi-volatile compounds that would condense inside a valve held at 200° C. However, special heating configurations can be employed that allow the wetted valve parts to be at temperatures greater than 200° C. while the actuating mechanism is kept at temperatures less than 200° C. (Seeley, J. V., et al., Anal Chem 72 4346 (2000); and Sinha, A. E., et al., J Chromatogr A 983 195 (2003)). This increases the temperature limit of the technique, but the current maximum temperature of a published diaphragm valve separation is 240° C. (Sinha, A. E., et al., J Chromatogr A 983 195 (2003)).

Pressure and flow fluctuations produced by valve switching are a third problem associated with diaphragm valve modulation. Fluctuations are produced when the secondary column head pressure is much greater than the pressure of the sample loop. Upon switching the valve from the fill to the flush position, the volumetric flow rate of the gas entering the secondary column temporarily decreases as the sample loop is brought up to the proper secondary column head pressure. Fortunately, the current practice of using long secondary columns (5 m) dampens the flow fluctuations and losses in chromatographic resolution have not been observed (Seeley, J. V., et al., Anal Chem 72 4346 (2000)). However, it is possible that fluctuations would lead to degraded resolution if short secondary columns were used.

The following is a detailed description of prior art devices have been developed for chromatographic analysis and flow injection analysis.

1. Multi-Port, Two-Position Valve With Direct Injection

Multi-port, two-position valves have been used extensively for injecting sample flow into a stream of pure gas. A schematic of a device that uses a 4-port valve is shown in FIGS. 1A and 1B. When the valve is in the "bypass" position the sample flow $F_S$ is directed to the exhaust while the pure gas flow $F_P$ is directed to the analytical device. When the valve is in the "inject" position, $F_S$ is directed to the analytical device while $F_P$ is sent to the exhaust. A pulse of sample gas in a stream of pure gas is generated by quickly switching the valve from the "bypass" position to the "inject" position and then back to the "bypass" position.

Key Performance Issues
- Pressure and Flow Fluctuations: If the flows $F_S$ and $F_P$ are not equal and/or the flow resistance of the tubes leading to the analytical device and the exhaust are not equal then all of the flows will experience a disturbance upon switching the valve.
- Sample Transfer: A pulse is delivered to the analytical device only when a small fraction of $F_S$ is sampled. This limits the sensitivity of component detection and limits the precision component transfer if the composition of FS changes with time.
- Temperature Range: The sample flow must pass through the multi-port valve. Currently, diaphragm valves are the only commercially available multi-port valves capable of continuous switching at a rate of 1 Hz. Such valves have upper temperature limits of 200° C. This reduces the range of samples that can be analyzed with such a device. For example, diesel fuel contains semi-volatile compounds that would condense inside a valve held at 200° C.
- Cost and Availability: The diaphragm valves used for this type of sampling often cost near $1000. VICI (Houston, Tex.) makes suitable diaphragm valves.

2. Deans Switch

The limitations of the multi-port two-position valve are partially addressed by the Deans switch. A schematic of such a device is shown in FIGS. 2A and 2B. The Deans switch uses a three-way valve to control the injection point of the pure gas flow. The sample flow $F_S$ enters the device through a tee union in the center of the device. The pure gas flow $F_P$ enters the common port of a three-way valve. The flow $F_P$ exits the valve and travels to either one of two tee unions on the periphery of the device. The direction of travel is determined by the state of the three-way valve. If $F_P$ is just slightly greater than $F_S$ and the flow resistance of the tube leading to the exhaust and the resistance of the tube leading to the analytical device are equal, then a small portion of $F_P$, shown in the figure as $F_P'$, will direct the sample gas to the exhaust when the valve is in the position shown in the left half of the figure. When the valve is switched to the position shown in the right half of the figure, $F_P'$ will direct the sample gas to the analytical device. A pulse of sample gas in a stream of pure gas is generated by quickly switching the valve from the "bypass" position to the "inject" position and then back to the "bypass" position.

Key Performance Issues
- Pressure and Flow Fluctuations: If a high speed valve is used and the size of the Deans switch is minimized, the disturbances to the incoming and outgoing flows are quite small.
- Sample Transfer: Like direct injection with a multi-port valve, the portion of the sample that reaches the analytical device is small. Unlike the multi-port valve, sample dilution can be significant (and undesirable) if $F_P'$ is not substantially smaller than $F_S$.
- Temperature Range: All of the moving parts of the device are in the valve. The sample flow does not pass through the valve. Thus, the valve can be housed in a zone of different temperature than the portion of the device that contacts the sample. This means a much broader range of temperatures is available to this technique than techniques employing a multi-port valve.
- Cost and Availability: The cost of a Deans Switch is less than a multi-port valve. However, such devices must often be constructed by the user.

3. Multi-Port, Two-Position Valve With Sample Loop(s)

A multi-port, two-position valve can be fitted with a sample loop to allow a greater amount of sample to be delivered to the analytical device. A schematic of a typical configuration employing a 6-port valve is shown in FIGS. 3A and 3B. Similar devices have been fabricated with 8-port and 10-port valves. When the valve is in the "load" position the sample flow FS is directed into the sample loop (shown as the diagonal line in the figure) while the pure gas flow FP is directed to the analytical device. When the valve is in the "inject" position the $F_S$ is directed to the exhaust while $F_P$ flushes out the sample loop to send its contents to the analytical device. If $F_S$ and $F_P$ are equal, then the time required to flush the loop is the same as the time required to fill the loop. However if the $F_P$ is greater than the $F_S$ then the loop will be flushed in less time than it was filled. In practice, a $F_P$ to $F_S$ ratio of approximately 20 is often used. Thus, a sample flow that is collected for 1.0 s can be injected into to analytical device as a 50 ms wide pulse. After the loops are flushed the valve is returned to the "load" position to begin collecting more sample flow. This approach of using a high flow of pure gas to achieve sample "compression in time" has been called differential flow modulation.

Key Performance Issues
- Pressure and Flow Fluctuations: Short but substantial pressure and flow fluctuations are possible when the pressure required to sustain the flow $F_P$ through the analytical device is much greater than the pressure required to sustain the flow $F_S$ to the exhaust Under such conditions, the sample loop will be at a lower pressure during the load phase. Upon switching to the inject position, the flow exiting the valve and heading to the analytical device will decrease as the sample loop is brought up to the pressure required to sustain a flow of $F_P$.
- Sample Transfer: A much greater portion of the sample can be sent to the analytical device under differential flow conditions because the valve can be kept in the load position for the majority of the time (this is because it takes much less time to flush the loop than fill the loop).
- Temperature Range: The sample flow must pass through the multi-port valve. Multi-port valves capable of continuous switching at a rate of 1 Hz are often diaphragm valves. Such valves have upper temperature limits of 200° C. This reduces the range of samples that can be analyzed with such a device. For example, diesel fuel contains semi-volatile compounds that would condense inside a valve held at 200° C.
- Cost and Availability: The diaphragm valves used for this type of sampling often cost near $1000. VICI (Houston, Tex.) makes suitable diaphragm valves.

OBJECTS

The object of the present invention is to provide a device which introduces a segment of fluid containing sample components into a flow of pure gas. The preferred device which injects the sample components as a short pulse, maximizes the amount of sample injected, which minimizes the disturbances to all of the gas flows (i.e., the sample gas flow, the pure gas flow, and the flow to the analytical device), and which is capable of consistently repeating this process at a frequency of approximately 1 Hz. It is further an object of the present invention to provide a device which is relatively low in cost and reliable. These and other objects will become increasingly apparent by reference to the following description and the drawings.

SUMMARY OF THE INVENTION

The present invention relates to a fluidic switching device which comprises: a valve comprising a single inlet adapted for receiving a carrier fluid and two outlets wherein the valve is actuated by an actuator for cycling between each of the outlets; first and second tubular conduits leading from the valve to each of two separate inlets into a common first union with an outlet between the inlets; third and fourth tubular conduits as a connection between the first and second tubular conduits; and a second union between the third and fourth tubular conduits adapted for flow between arms of the union and adapted so that a fluid can flow into two arms from a leg of the second union, wherein the device is constructed so that fluid flow is greater in the first and second conduits than in the third and fourth conduits such that when the flow is switched in the valve to the one of the first or second conduits a fluid material introduced in the second union is temporarily accumulated in the opposite first or second conduit from the third or the fourth conduit which is subsequently flushed from the opposite first or second conduit by the carrier fluid flowing in the opposite first or second conduit upon switching of the valve from one of the outlets from the valve to the other outlet from the valve.

Further, the present invention relates to a fluidic switching device which comprises: a valve comprising a single inlet adapted for receiving a carrier fluid and two outlets wherein the valve is actuated by an actuator for cycling between each of the outlets; first and second tubular conduits of equal internal flow resistance leading from the valve to each of two separate inlets into a common first union with an outlet between the inlets; third and fourth tubular conduits of equal internal flow resistance as a connection between the first and second tubular conduits; and a second union between the third and fourth tubular conduits adapted for flow between arms of the union and adapted so that a fluid can flow into two arms from a leg of the second union, wherein the device is constructed so that fluid flow is greater in the first and second conduits than in the third and fourth conduits such that when the flow is switched in the valve to the one of the first or second conduits a fluid material introduced in the second union is temporarily accumulated in the opposite first or second conduit from the third or the fourth conduit which is subsequently flushed from the opposite first or second conduit by the carrier fluid flowing in the opposite first or second conduit upon switching of the valve from one of the outlets from the valve to the other outlet from the valve.

Still further, the present invention relates to a chromatographic separator apparatus which comprises: a fluidic switching device as set forth above and at least one chromatographic column connected to the leg of the second union; wherein the device is adapted to move units of the fluid material mixed with the carrier fluid into the column between units of the carrier fluid alone.

Finally, the present invention relates to a method for fluidic switching which comprises: providing a fluidic switching device as set forth above; and introducing the carrier fluid into the inlet of the valve and the fluid material into the inlet into the second union wherein the valve delivers units of the fluid material mixed with the carrier fluid between units of the carrier fluid to the outlet of the first union.

A multi-port, two-position valve can be fitted with two external sample loops to allow differential flow modulation to be performed with minimal flow disturbances and 100% transfer of sample components to the analytical device. A schematic of an appropriate device that could use a 4-port valve is shown in FIGS. 4A and 4B. The each sample loop is connected to a port on the valve. The two sample loops are joined together with a tee union. When the valve is in the position shown on the left side of the figure, the sample flow $F_S$, fills the loop on the left side of the valve while the pure gas flow, $F_P$, flushes the loop on the right side of the valve. When the valve is switched, the sample flow, $F_S$, fills the loop on the right side of the valve while the pure gas flow, $F_P$, flushes the loop on the left side of the valve. If $F_P$ is substantially greater than $F_S$ and the loop is switched prior to the point when $F_S$ would over-fill the sample loops, then all of $F_S$ will pass to the analytical device as series of sample pulses. This device is not preferred.

BRIEF DESCRIPTION OF THE DRAWINGS

FIGS. 1A and 1B are schematic diagrams of a 4-port valve used for direct injection of sample gas into a stream of pure gas. The two possible states of the valve are shown.

FIGS. 3A and 3B are schematic diagrams of a multi-port valve used for differential flow injection of sample gas into a stream of pure gas. The two possible states of the device are shown. The sample loop is shown as the diagonal line across the center of the device.

DESCRIPTION OF PREFERRED EMBODIMENTS

The device of the present invention allows a flow of a sample gas containing one or more chemical components at trace levels to be combined with a larger flow of a pure gas. The combined flow of gas that exits the device has alternating and distinct segments of each fluid stream; i.e., the exiting flow is a series of short segments of sample gas between larger segments of pure gas with minimal mixing between the segments. The essential result is that the device takes an incoming sample flow and converts it into a series of sample pulses. The device is designed to produce minimal disturbances to the incoming and outgoing fluid streams.

An embodiment of this invention has been assembled from six pieces of tubing, four tee unions, and a solenoid valve. The device was successfully employed in the production of differential flow modulation comprehensive two-dimensional gas chromatographic separations. The function of the device for this particular application was to convert the peaks emerging from the primary column into a series of pulses that are subsequently injected into two secondary columns. In particular application, the device replaces a 6-port valve fitted with a sampling loop. The device is superior to a 6-port valve because it works at a wider range of temperatures, costs less, and produces smaller flow disturbances.

The present invention provides a new modulation device that allows differential flow GC×GC separations to be performed without diaphragm valves. The device is related to previously published flow switching devices (Deans, D. R., Chromatographia 118 (1968); and Sacks, R., et al., Environmental Science and Technology 28 428A (1994))) in that flow directions are controlled by a three-port solenoid valve located outside of the column oven and not in the sample path. The portion of the modulation device inside the oven contains no moving parts and is constructed with material that can withstand a wide range of temperatures. In addition, the device employs very small pressure differences to produce modulation. Thus, flow disturbances to the primary and secondary columns are minimized. This invention is divided into two parts: a theoretical analysis of the flow-switching device and an experimental validation of the device as a GC×GC modulator.

Figure 5:
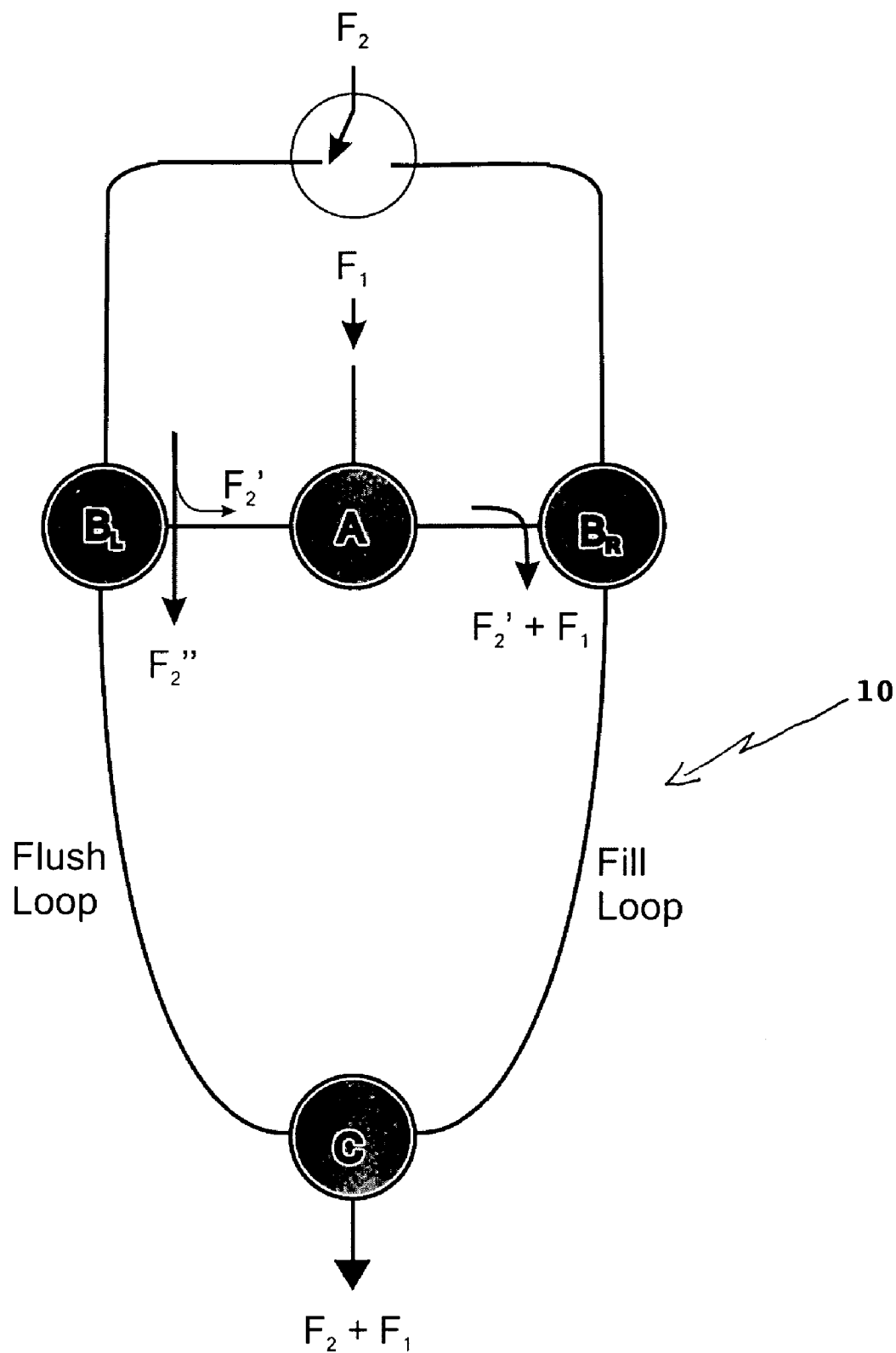
FIG. 5 is a schematic view of the preferred fluidic device of the present invention wherein $F_2$ is the carrier fluid and $F_2$ is the fluid material or sample. A and C are unions and $B_L$ (Left) and $B_R$ are T connectors which are all connected by conduits or tubing.
Figure 6:
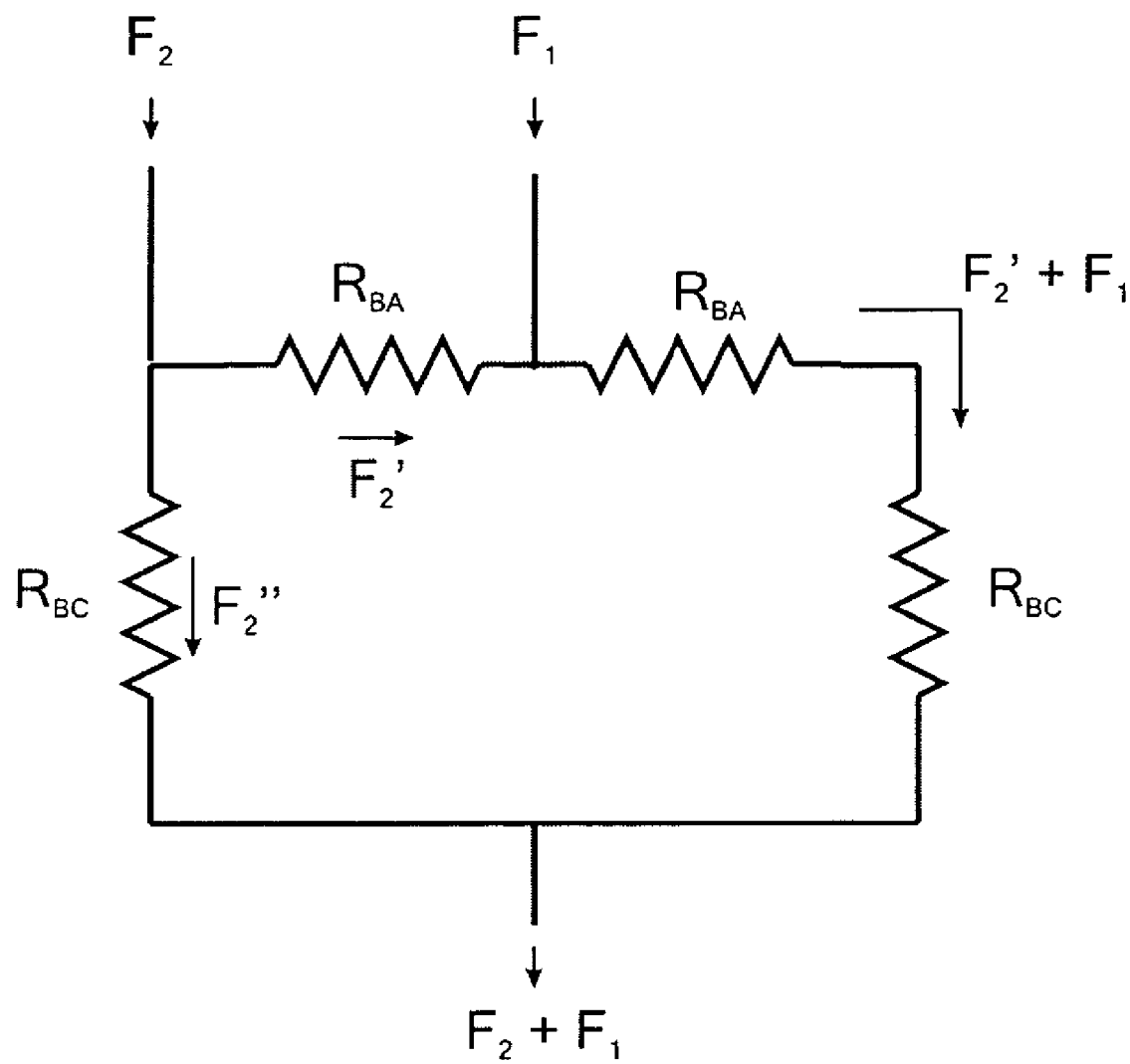
FIG. 6 is an equivalent flow diagram for the flow of the fluid.
Figure 7:
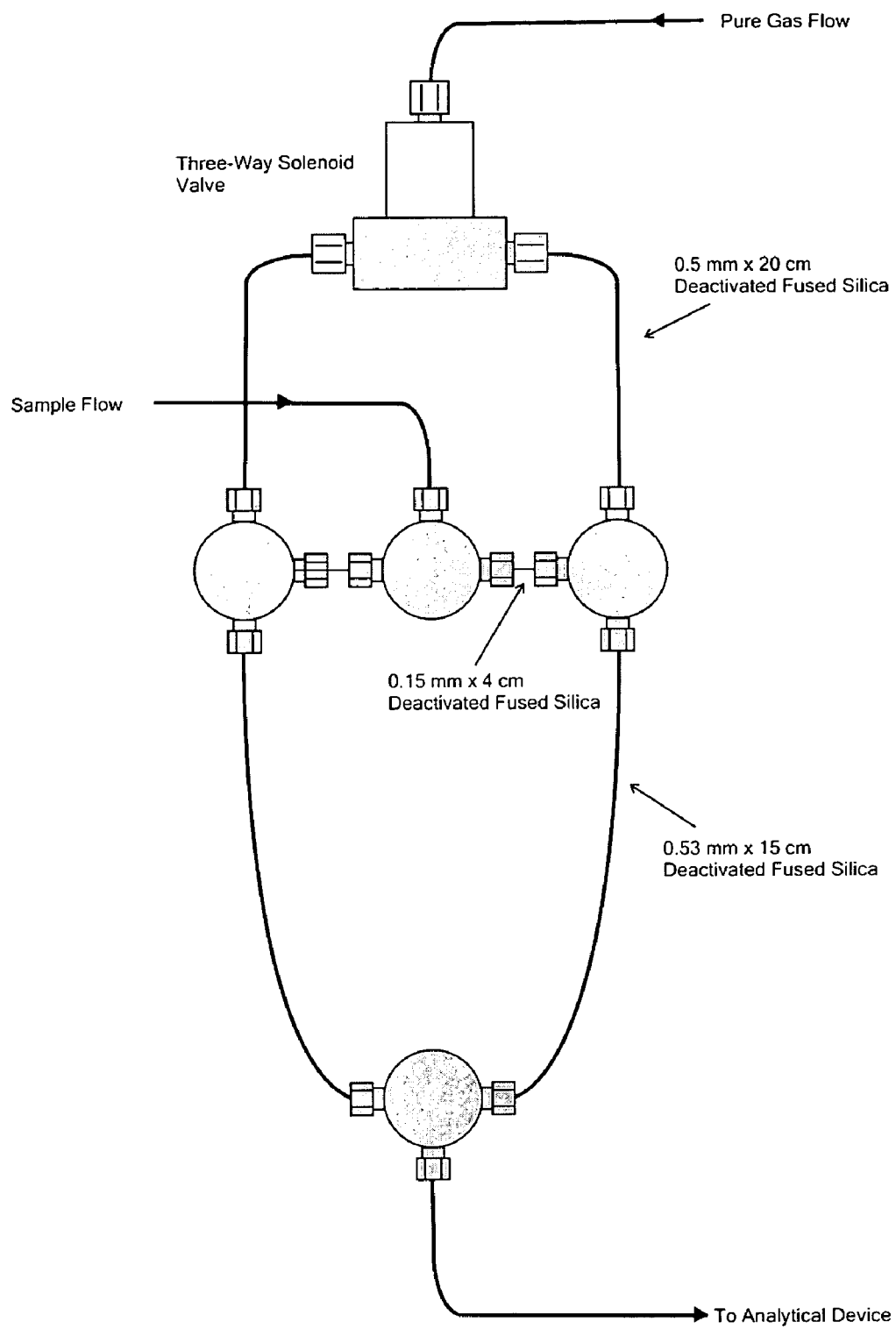
FIG. 7 is a representational diagram of the device 10 of FIG. 5 of the present invention used for chromatographic studies.

A schematic of the device is shown in FIG. 5 and the actual device is shown in FIG. 7. The flow exiting the primary column, $F_S$, enters the device at union A. Union A is connected to two peripheral unions, $B_L$ and $B_R$, with pieces of tubing having the same dimensions (i.e, the same length and internal diameter). An auxiliary flow of carrier gas, $F_P$, enters the common port of a three-port valve. This flow is substantially greater than the primary column flow. The auxiliary flow exits the three-port valve and travels to either union $B_L$ or union $B_R$. The direction of travel is determined by the state of the three-port valve. The pieces of tubing extending from the valve to the unions $B_L$ and $B_R$ have the same dimensions. The unions $B_L$ and $B_R$ are also connected to union C. The tubing extending from $B_L$ to C has the same dimensions as the tubing from $B_R$ to C. These two pieces of tubing serve as collection loops for primary column effluent. The flow $F_S$ and $F_P$ exit the device through union C to enter the secondary column.

The device uses the auxiliary flow $F_2$ to guide the primary column effluent into one of the collection tubes while simultaneously flushing out the other collection tube. For instance, when the three-port valve is in the position shown in FIG. 5, a small portion of $F_2$ (shown as $F_2'$) directs the primary column effluent to the right sample loop (i.e., the tube between $B_R$ and C) while the remainder of $F_2$ (shown as $F_2''$) flushes out the left sample loop (i.e., the tube between $B_L$ and C). When the valve is switched to the opposite position (not shown in the figure), $F_2'$ emerges from union $B_R$ and pushes the primary column effluent to the left sample loop while the remainder of $F_2$ flushes out the right sample loop. Switching the three-port valve at regular intervals will result in a series of pulses of primary column effluent exiting the device through union C. Optimal modulation is predicted when $F_2'$ is just large enough to direct the primary column effluent into the sample loop. Higher values of $F_2'$ would be counter-productive as they would dilute the primary column effluent and broaden the resulting pulses.

Creating conditions where $F_2'$ is smaller than $F_1$ (but still greater than zero) requires proper proportioning of the flow resistances within the device. It is useful to derive an equation that predicts how $F_2'$ is related to the flows $F_2$ and $F_1$ and the resistances within the device. The following derivation assumes that the change in pressure between the center of any two unions, $\Delta P$, follows an Ohm's Law form; i.e., $\Delta P = F \cdot R$ where F is the volumetric flow rate between the two unions and R is the resistance to flow. This equation is a good approximation when the pressure change across any two unions is substantially smaller than the average pressure (Giddings, J. C., Unified Separation Science, Wiley, New York (1991)).

The device is represented in the form of a resistor diagram in FIG. 3. The flow resistance from union $B_L$ to union A is assumed to be the same as the resistance from union $B_R$ to union A. These resistances are denoted as $R_{BA}$. The resistance from union $B_L$ to union C is assumed to be the same as the resistance from union $B_R$ to union C. These resistances are denoted as $R_{BC}$.

The derivation starts with the assertion that the pressure drop from the center of union $B_L$ to the center of union C along the tube directly connecting $B_L$ to C is the same as the pressure drop along the path of union $B_L$ to union A to union $B_R$ to union C. Thus, equating the pressure drops along these two paths produces $$F_2''R_{BC} = F_2'R_{BA} + (F_2' + F_1)(R_{BA} + R_{BC})$$

Using $F_2'' = F_2 - F_2'$, this equation can be rewritten as $$F_1(R_{BA} + R_{BC}) + 2 F_2'(R_{BA} + R_{BC}) - F_2 R_{BC} = 0$$

Upon further rearrangement, this equation gives $$F_2'/F_2 = \tfrac{1}{2}[R_{BC}/(R_{BA} + R_{BC}) - F_1/F_2] \quad (1)$$

Optimal differential flow modulation will be produced when $F_2'$ is greater than zero but substantially smaller than both $F_1$ and $F_2$. Such a condition is produced when the right side of equation 1 is positive but close to zero. This is achieved when $R_{BC}/(R_{BA} + R_{BC})$ is just slightly greater than $F_1/F_2$. Equivalently, this corresponds to the case when $R_{BA}/R_{BC}$ is slightly less than $(F_2/F_1) - 1$.

In addition to resistance restrictions, proper operation of the device can only be achieved if the volumes of the tubes that connect the union A to the unions $B_L$ and $B_R$ are minimized, while the volumes of the sample loops (i.e., the pieces of tubing that connecting $B_R$ to C and $B_L$ to C) are large enough to hold the primary column effluent during the desired sampling period. This requirement can be satisfied by using short tubes with small internal diameters to connect union A to the peripheral unions and long tubes with larger diameters to connect the peripheral unions to union C.

It is now estimated that the dimensions of tubing that would produce optimal modulation for the case of $F_1 = 1$ cm$^3$ min$^{-1}$, $F_2 = 20$ cm$^3$ min$^{-1}$, and a switching frequency is 0.5 Hz. If tubing with an internal diameter of 0.53 mm is used as the sample loops, the volume of each of these tubes needs to be at least the volume delivered by $F_1$ in the 2 s collection period. For a flow of 1 cm$^3$ min$^{-1}$ this corresponds to 0.0333 cm$^3$. Approximately 15 cm of 0.53 mm i.d. tubing is necessary to hold this volume. With the dimensions of the sample loops determined, we now estimate the dimensions of tubing between the A and B unions that would properly balance the resistance of the sample loops. In this particular case, $F_2/F_1$ is 20 so optimal modulation performance is predicted when $R_{BA}/R_{BC}$ is slightly less than 19. The Poiseuille equation for laminar flow predicts that the flow resistance of tubing is inversely proportional to the fourth power of the internal diameter (Giddings, J. C., Unified Separation Science, Wiley, New York (1991)). Thus, 0.15 mm i.d. tubing is 156 times more flow resistant than the 0.53 mm tubing per unit length. Therefore a $R_{BA}/R_{BC}$ ratio of 19 can be generated using 1.8 cm pieces of 0.15 mm i.d. tubing to connect union A to $B_R$ and $B_L$. This result shows that adequate resistance can be generated without creating a large volume between the A and B unions: The internal volumes of the pieces of tubing that connecting union A to the peripheral unions are less than 2% of the volume of the sample loops.

The previous analysis assumes that the flow resistances are determined completely by the pieces of tubing within the device. In practice we have found that the unions make a significant contribution (approximately 30%) to the sample loop resistance. Thus, slightly longer tubes between the union A to the peripheral unions are needed to properly balance the device. The key result of these calculations is that they demonstrate that a flow-switching device can be constructed with readily available materials (i.e., unions and tubing of standard dimensions) and that the size of the resulting device will easily fit inside a gas chromatograph.

EXAMPLE 1

General Setup

Figure 9:
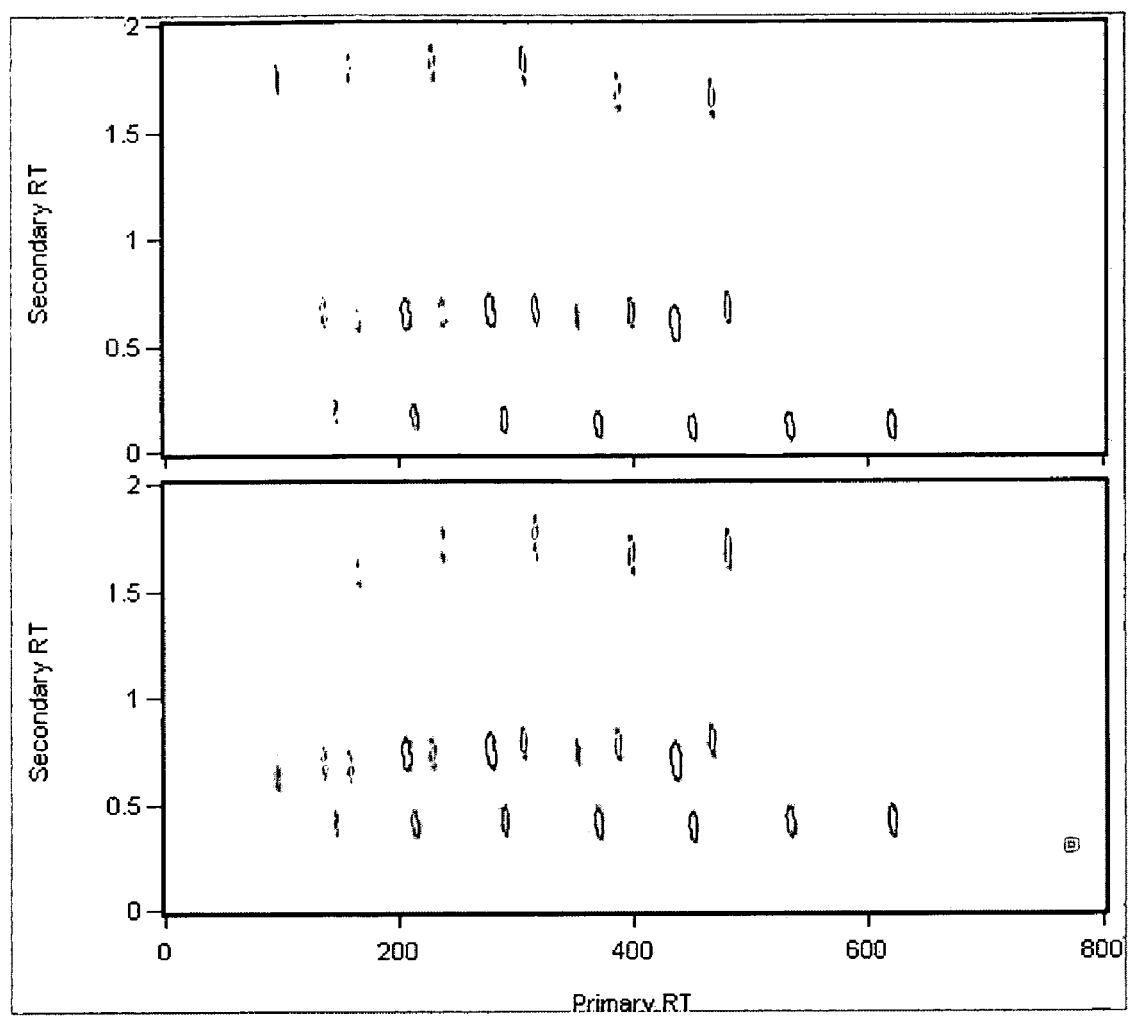
FIG. 9 is a two-dimensional gas chromatograph produced by the device of FIG. 8.

A schematic of the GC×2GC system is shown in FIG. 9, which is enclosed in an oven, was used. A Perkin-Elmer (Norwalk, Conn., USA) Autosystem XL gas chromatograph with electronic pneumatics and dual flame-ionization detectors (FIDs) was used as the experimental platform. Ultra-high purity hydrogen was used as the carrier gas in the primary and secondary columns. Neat mixtures were injected into the primary column through a split inlet (30:1 split ratio). The flow exiting the switching device was divided between two secondary columns with a tee union. Effluent from each secondary column was passed through a flame-ionization detector (FID). The 100 nF filtering capacitor on each FID electrometer was replaced by an 8 nF capacitor. The signals from the detectors were monitored at 200 Hz by a personal computer equipped with a data acquisition board and custom software. The capillary columns used in these studies can be purchased from Agilent Technologies (Folsom, Calif., USA).

The Switching Device

A drawing of the flow-switching device 10 is shown in FIG. 7. The device 10 includes a 3-way solenoid valve 11, silica tubing 12 and unions 13, 14, 15 and 16.

Figure 8:
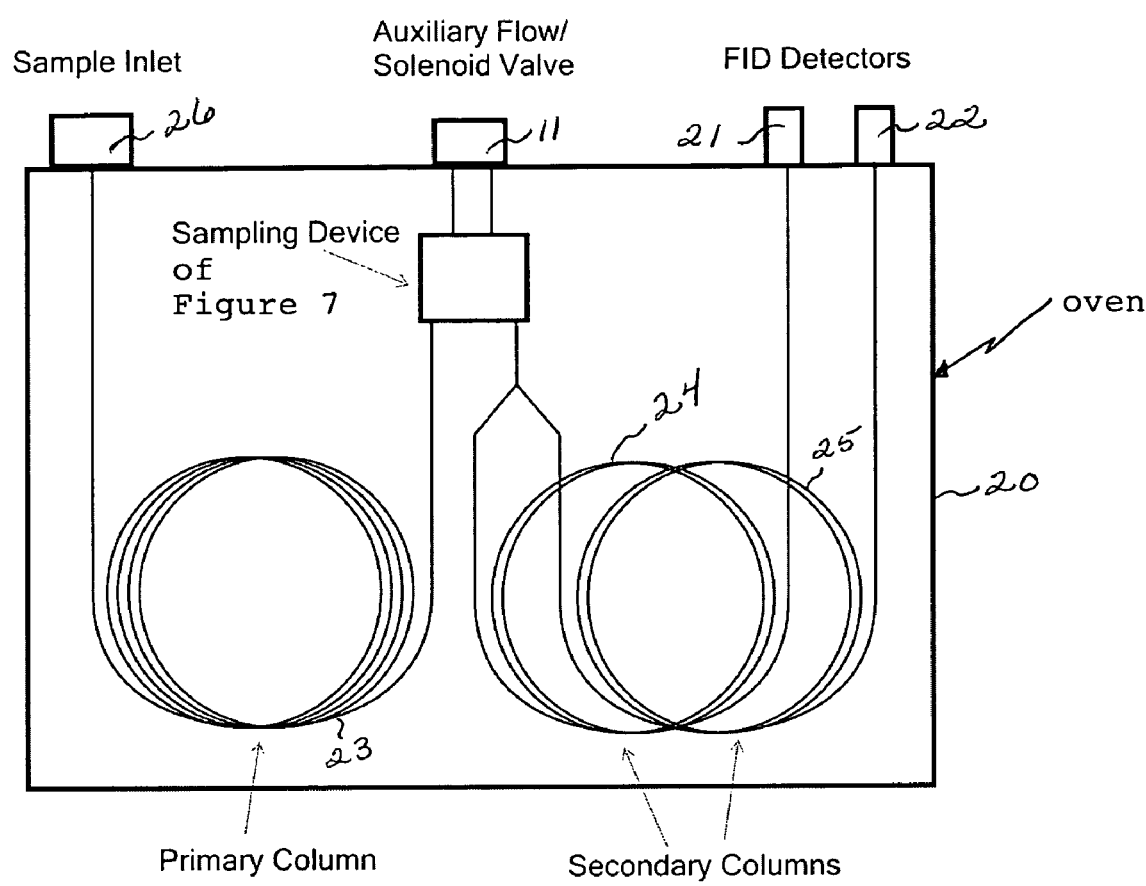
FIG. 8 is a schematic diagram of a two-dimensional gas chromatograph apparatus of the present invention wherein the fluidic switching device is in an oven 20 except for the valve 11.

The device 10 is mounted in a steel plate (not shown) inside of an oven 20 as shown in FIG. 8. The solenoid valve 11 is mounted outside of the oven as are the flame detectors 21 and 22 (FIG. 8). The primary column 23 and secondary columns 24 and 25 are inside of the oven 20. A sample is introduced at a port 26.

The device was constructed with deactivated fused silica tubing, stainless steel tubing, four "T" unions (stainless steel, 0.25 mm i.d. orifices, VICI, Houston, Tex., USA, part number MT.5CS6), and a three-port solenoid valve (Parker-General Valve, Fairfield, N.J., USA, part number 009-0284-900). An auxiliary flow of carrier gas was connected to the common port of the 3-port solenoid valve. The solenoid valve was positioned on the top of the chromatograph outside of the oven. The remainder of flow switching device was mounted on a thin piece of stainless steel sheet and housed inside the column oven. The output ports of the solenoid valve were connected to the peripheral unions of the switching device with two pieces of stainless steel tubing (20 cm length, 0.5 mm i.d.). The exit of the primary column was connected to the center union. The center union was connected to the peripheral unions with two pieces of deactivated fused silica capillary tubing (2.7 cm long, 0.15 mm i.d. for the volatile organic compound studies; 4.0 cm long, 0.15 mm i.d. for the diesel fuel studies). The peripheral unions were connected to the lower union with two pieces of deactivated fused silica capillary tubing (15 cm long, 0.53 mm i.d.). The primary column flow and auxiliary flow exited the device through the lower union. During operation, the solenoid valve was switched every 2 s by a computer controlled circuit. Switching the solenoid valve did not produce observable pressure or flow fluctuations at the head of the primary column, the auxiliary flow controller, or the exit of the secondary columns.

Volatile Organic Compound Studies

Neat mixtures of volatile organic compounds (VOCs) were injected in 0.05 μL quantities. The primary column flow was 0.80 mL min$^{-1}$ and the auxiliary flow was 20.0 ml min$^{-1}$. The oven temperature was ramped according to the following program: 40° C. for 1.0 min, ramp to 75° C. at 14.0 K min$^{-1}$, ramp to 120° C. at 10.0 K min$^{-1}$, ramp to 160° C. at 6.5 K min$^{-1}$, hold for 1.0 min. A 5.0 m×250 μm DB-624 capillary column (6% cyanopropylphenyl, 94% dimethyl polysiloxane, 1.4 μm film thickness) was used as the primary column. A 5.2 m×250 μm DB-Wax column (polyethylene glycol, 0.10 μm film thickness) and a 5.2 m×250 μm DB-210 column (trifluoropropylmethyl-polysiloxane, 0.25 μm film thickness) were used as the secondary columns. Measurements of the flow exiting from each secondary column indicated that the secondary flow was evenly split to within 2%.

Diesel Fuel Studies

A sample of diesel fuel was obtained from a local service station and injected in 0.5 μL quantities. The primary column flow was 0.90 mL min$^{-1}$ and the auxiliary flow was 26.4 ml min$^{-1}$. The oven temperature was ramped according to the following program: 50° C. for 1.5 min, ramp to 240° C. at 12.5 K min$^{-1}$, hold for 6.0 min. A 27.0 m×250 μm HP-5 capillary column (5% diphenyl, 95% dimethyl polysiloxane, 0.25 μm film thickness) was used as the primary column. A 5.7 m×250 μm DB-Wax column (polyethylene glycol, 0.10 μm film thickness) and a 1.4 m×250 μm deactivated fused silica column were used as the secondary columns. Measurements of the flow exiting from the secondary columns indicated that the secondary flow was split in a 1:4 ratio between the DB-Wax secondary column and the deactivated fused silica column.

Results and Discussion

Volatile Organic Compound Studies

Figure 10:
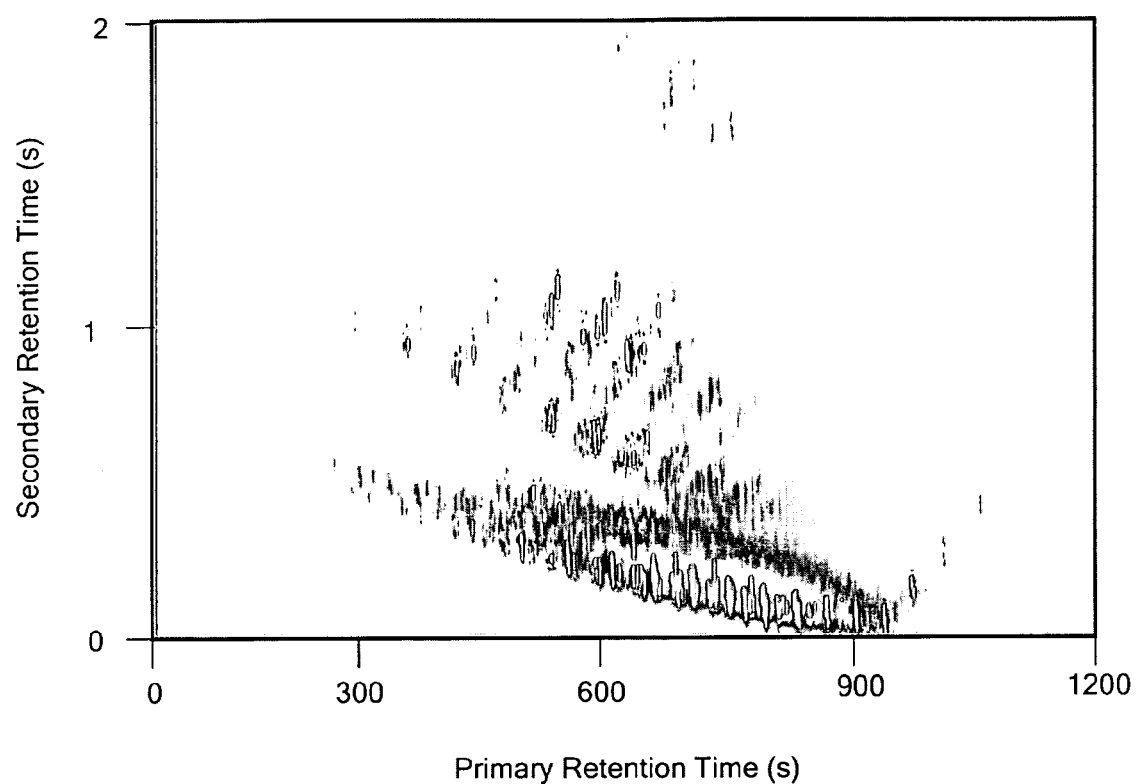
FIG. 10 is a chromatograph of diesel fuel produced by the device of FIG. 8.
Figure 11:
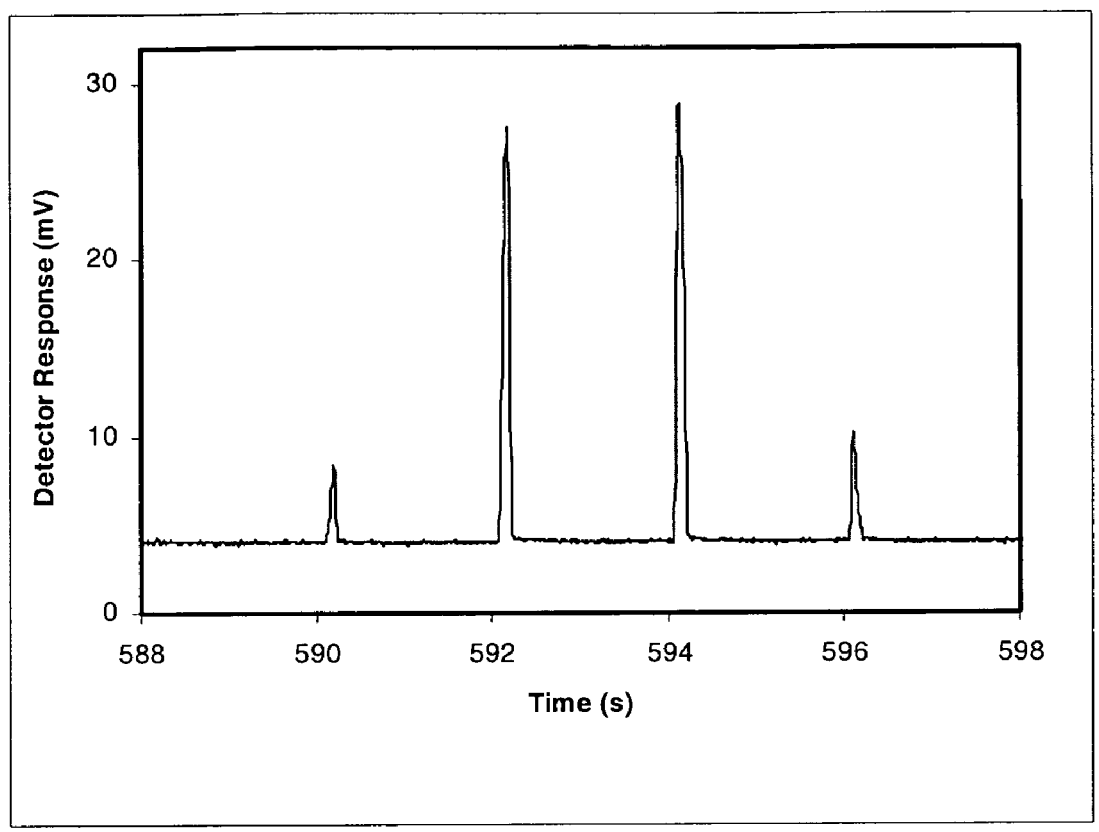
FIG. 11 is a graph showing a one dimensional signal from the DB-Wax detector. The peaks shown are due to dodecane and have widths at a maximum of 90 ms.

The experimental configuration used for the volatile organic compounds (VOCs) studies is similar to the setup of our previous GC×2GC studies performed with a 6-port diaphragm valve (Seeley, J. V., et al., J Sep Sci 24 444 (2001)). A 41-component mixture was used as a test mixture. This mixture contained the following VOCs: $C_5$-$C_{14}$ n-alkanes, $C_1$-$C_8$ 1-alcohols, $C_3$-$C_8$ 2-alcohols, $C_3$-$C_8$ and $C_{10}$ acetates, $C_3$-$C_8$ 2-ketones, and $C_7$-$C_{10}$ alkyl aromatics. Compounds within each functional class differed only by the length of their straight-chain alkyl group. The 2-D chromatograms for this mixture are shown in FIG. 10. In general, the chromatograms produced by the flow switching device are similar to those obtained with diaphragm valve modulation. FIG. 11 contains a portion of the signal array recorded from the detector connected to the DB-Wax secondary column. The dodecane peaks are displayed. The width at half maximum of the peaks are 90 ms. Similar widths were observed for all compounds that were poorly retained on the secondary columns. Highly retained peaks, such as the primary alcohols in the DB-Wax chromatogram, had peak widths at half maximum of approximately 110 ms.

Perfect differential flow modulation with the 0.8 to 20 flow ratio and a 2 s modulation period will inject components into the secondary columns as 80 ms wide pulses. The observed peak widths are very close to this value indicating that the flow-switching device produces near optimal modulation. However, we also found the modulated peaks displayed tailing near the baseline. The degree of tailing was very small (see FIG. 11) but consistently present and not connected with compound polarity (e.g. injections of methane produced the same amount of tailing as primary alcohols). It is possible that this tailing is caused by dead volume within the switching device. Due to the small size of the tailing, we do not believe that it significantly degrades the chromatographic resolution.

Diesel Fuel Studies

Figure 12:
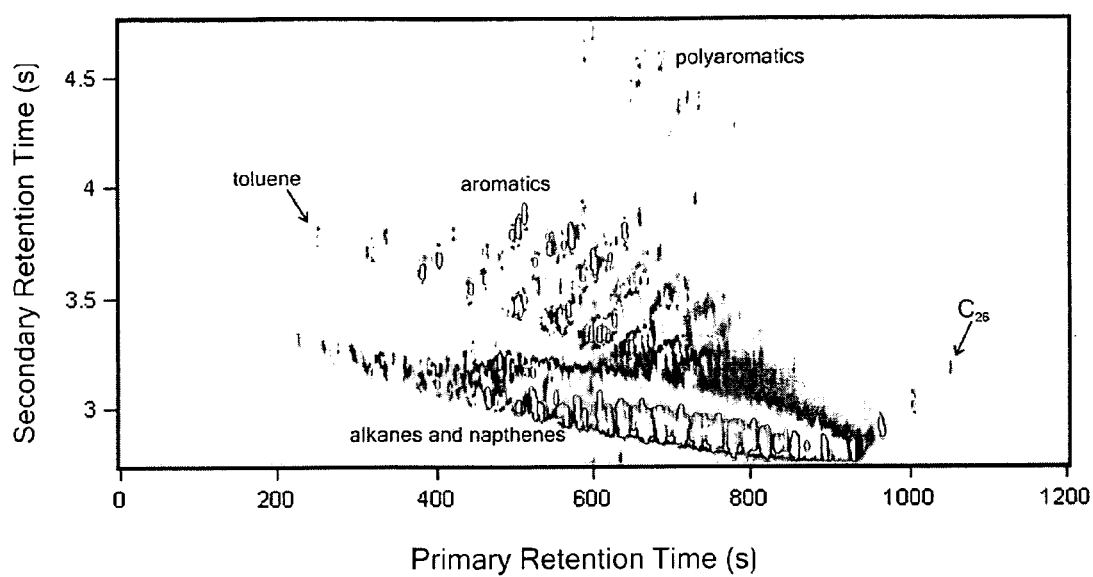
FIG. 12 is a two-dimensional gas chromatograph of diesel fuel using a DB-5 primary column and a DB-Wax secondary column.
Figure 13:
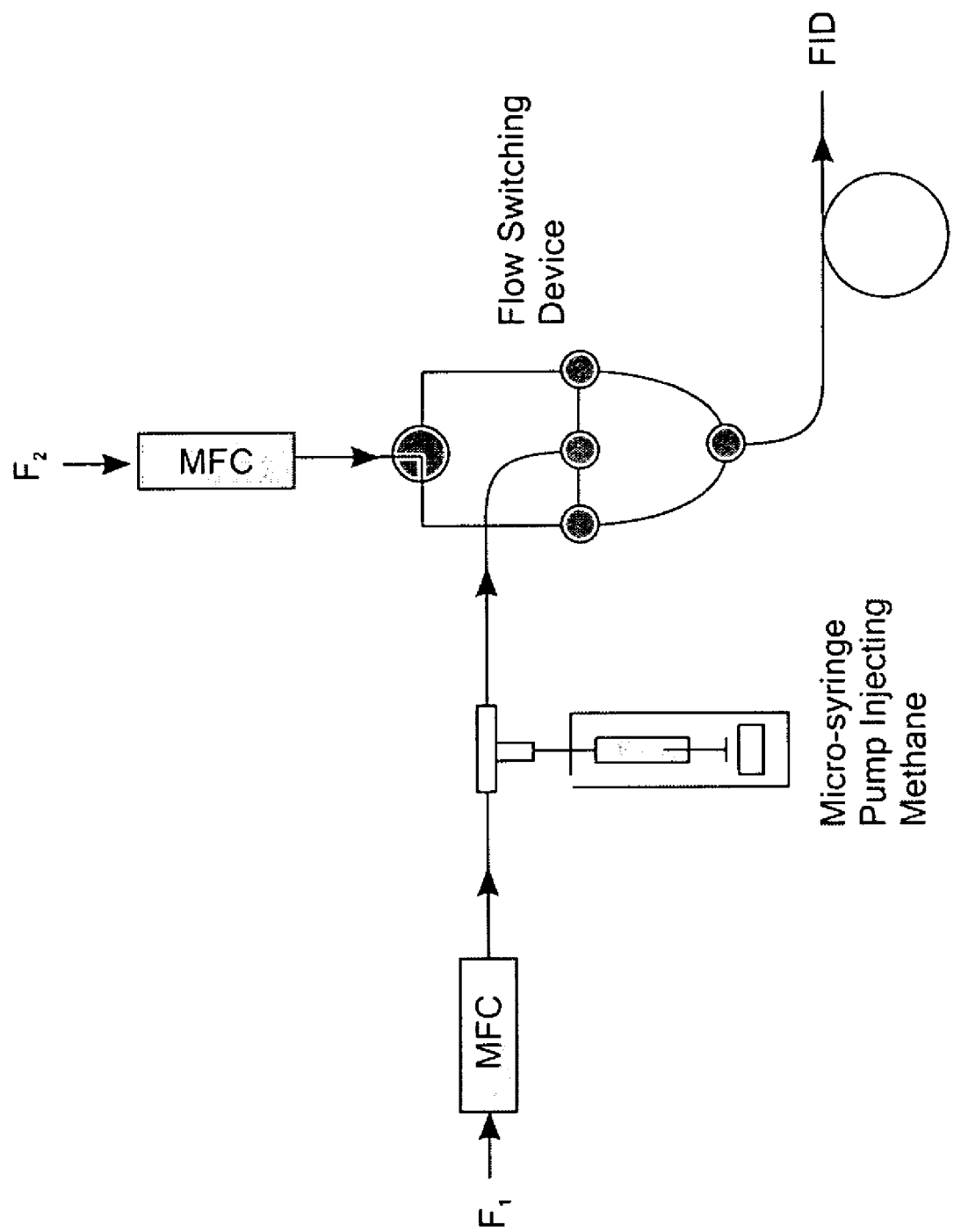
FIG. 13 is a schematic of the apparatus for the modulation of a constant composition mixture. The primary flow ($F_1$) and secondary flow ($F_2$) are independently set with mass flow controllers (MFC). A syringe pump is used to slowly add a trace of methane to the primary flow. The flow-switching device samples the primary flow. The resulting modulated flow is passed through a transfer line and into a flame ionization detector (FID).

Diesel fuel was analyzed to test the performance of the flow-switching device at higher temperatures. The 240° C. maximum temperature of the analysis was set by the temperature limit of the DB-Wax secondary column. A primary to secondary flow ratio of 0.90 to 26.4 was used. Slightly longer capillaries between the central union and the peripheral unions were used to accommodate a higher secondary flow. FIG. 12 contains a typical GC×GC chromatogram. The results are similar to diesel fuel separations obtained with thermal modulation and a secondary column containing polyethylene glycol (Gaines, R. B., et al., Environmental Science and Technology 33 2106 (1999)). All of the resolved peaks are very sharp along the secondary dimension, with widths at half maximum of approximately 70 ms. Once again, these widths are close to the theoretical limit imposed by a 0.90 to 26.4 flow ratio. The 1 to 4 splitting of the secondary flow after modulation was used to demonstrate how differential flow with post-modulation splitting can be used to sharpen peaks while still sampling the entire widths of peaks emerging from the primary column.

The flow-switching device performed well at high temperature. For example, the $C_{26}$ peak that eluted at a primary retention time of 1058 s and an oven temperature of 240° C. had the same width in the secondary dimension as the toluene peak that eluted at a primary retention time of 252 s and a temperature of 73° C.

This Example demonstrates that a flow switching device assembled from a few simple, commercially available components can generate high resolution GC×GC separations of volatile and semi-volatile compounds. The device has several advantages over diaphragm valve modulation. The most obvious is an extended upper temperature limit. With the flow-switching device, the upper temperature limit is dictated by the limitations of the capillary columns not the limitations of the modulator. In addition, the flow-switching device produces much smaller flow disturbances than diaphragm modulation, and the device samples all of the primary column effluent.

EXAMPLE 2

The goal of this Example was to determine the influence of experimental parameters, such as the primary flow rate, secondary flow rate, and device dimensions, on the performance of the flow-switching modulator. These parameters were investigated to determine how they influence the width and shape of modulated peaks. An apparatus was constructed that allows the primary and secondary flow rates to be controlled independently with high precision. In addition, the apparatus enabled the flow-switching device to be directly compared to multi-port valve modulation.

Theoretically, pulses of primary column effluent exit the device with temporal widths given by the ratio of the loop fill rate ($F_1+F_2'$) to the loop flush rate ($F_2''$) multiplied by the modulation period. Thus, the expected temporal width of an exiting pulse, w, is given by $$w = \frac{F_1 + F_2'}{F_2''}\tau = \frac{F_1 + F_2'}{F_2 - F_2'}\tau \quad (1)$$

where $\tau$ is the modulation period.

Inspection of Equation 1 shows that a minimum pulse width is obtained when the cross flow $F_2'$ approaches zero. Under such conditions, the width of the injected pulse is determined by the primary to secondary flow ratio and is given by $$w = \frac{F_1}{F_2}\tau \quad (2)$$

This width is the theoretical minimum for proper differential flow modulation.

While the minimum width would be obtained with $F_2'=0$, such a condition would not be ideal as the region between the union A and peripheral injection union would not be flushed. Thus, remnants of primary column effluent would be stored in the connecting capillary until the next modulation cycle. However, the impact of this effect would be small as the volume of the capillary joining unions A and B is less than 4% of the sample loop volume.

Operating under conditions where $F_2'$ is negative also results in poor performance. Although the width of the resulting pulses is narrower than the theoretical minimum, the cross flow $F_2'$ travels from union A to the peripheral injection union (instead of the proper direction from the peripheral injection union to the center union A). Thus, the primary column flow is not directed exclusively into the collection loop, but instead splits into two directions: a portion toward the collection loop and a portion toward the flushed loop. This causes the secondary flow flushing the loop to be contaminated with primary column effluent. As a result, narrow peaks are produced but the modulation is unacceptable because a substantial increase in the baseline is observed.

In principle, a properly tuned flow switching device (i.e., a device that generates a small but positive value of $F_2'$) should produce peaks with widths near the theoretical minimum without producing substantial baseline disturbances. The inability to generate such peaks would most likely be due to a poorly designed device (e.g., excessive dead-volumes, active surfaces, or leaks).

Figure 2A:
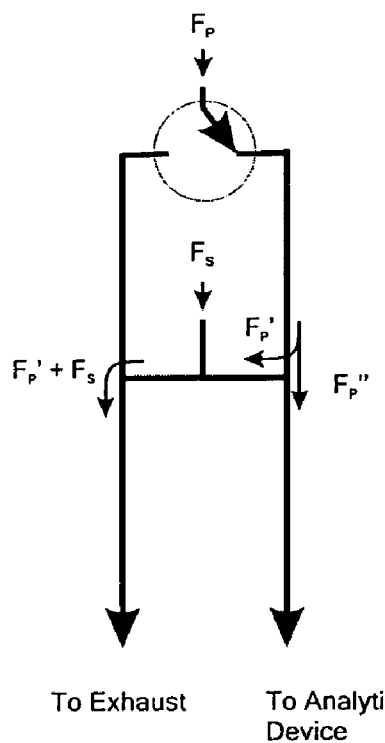
FIGS. 2A and 2B are schematic diagrams of a Deans switch used for direct injection of sample gas into a stream of pure gas. The two possible states of the device are shown.
Figure 2B:
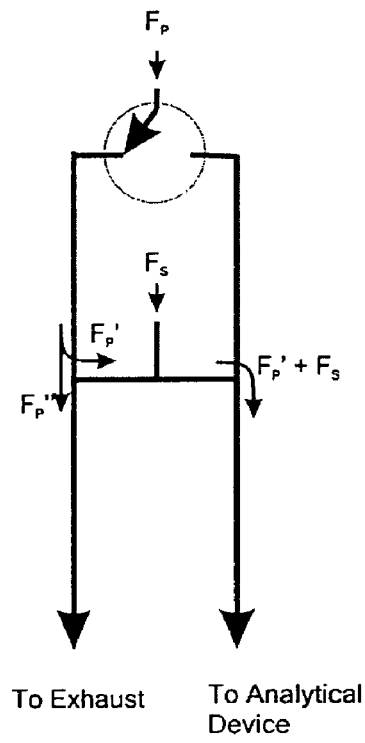
Figure 4A:
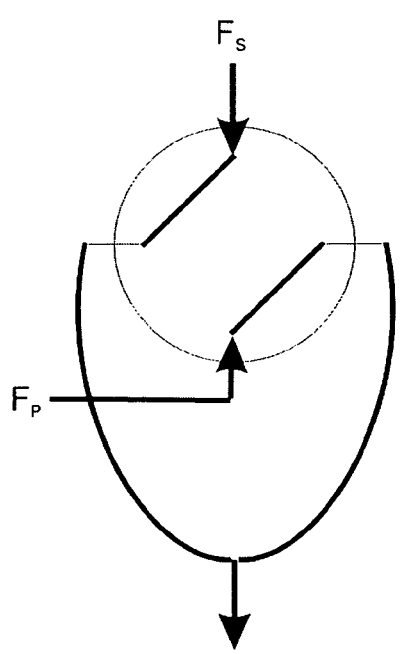
FIGS. 4A and 4B are schematic diagrams of a multiport two-position diaphragm valve with external loops. Load Left/Inject Right and Load Right and Inject Left for the device of the present invention.
Figure 4B:
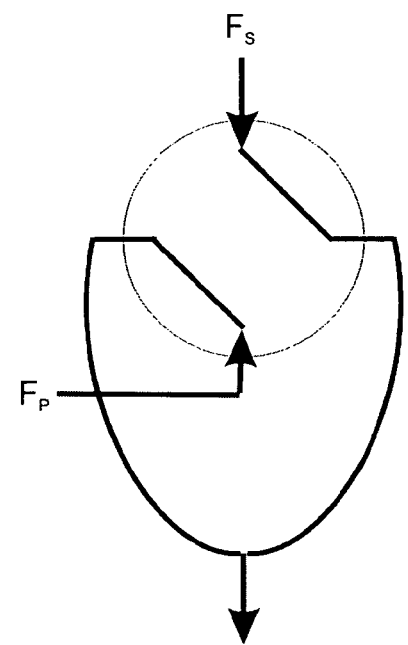

The performance of the flow switching device was studied by modulating a methane/hydrogen mixture. The schematic of the apparatus is shown in FIG. 2. Ultra-high purity hydrogen was used as the carrier gas. Electronic mass flow controllers (MKS Instruments, Andover, Mass.) were used to regulate the carrier gas flow rates. A 25 µL gas-tight syringe and a syringe pump (KD Scientific, New Hope, Pa., Model 100) were used to inject methane. A primary flow of 0.5 to 1.0 mL min$^{-1}$ was continuously mixed with a 1.5 µL min$^{-1}$ flow of methane. The resulting methane/H$_2$ mixture was introduced to the flow-switching device at the central union. A secondary flow of carrier gas ranging from 10 to 25 mL min$^{-1}$ was injected into the common inlet of the three-port solenoid valve of the switching device.

An expanded view of the flow-switching device is shown in FIG. 7. The device was constructed with deactivated fused silica tubing, four t-unions (stainless steel, 0.25 mm i.d. orifices, VICI, Houston, Tex., USA, part number MT.5CS6), and a three-port solenoid valve (Parker-General Valve, Fairfield, N.J., USA, part number 009-0284-900). The output ports of the solenoid valve were connected to the peripheral unions of the switching device with two pieces of 10.0 cm×530 µm deactivated fused silica tubing. The center union was connected to the peripheral unions with two pieces of 3.9 cm×150 µm deactivated fused silica tubing. The peripheral unions were connected to the lower union with two pieces of 15.0 cm×450 µm deactivated fused silica tubing. A computer-controlled circuit switched the solenoid valve. Valve switching did not produce observable fluctuations in the primary or secondary flows.

The flow emerging from the switching device was transferred to a flame-ionization detector (FID) via a 163 cm×250 µm deactivated fused silica column. The FID was housed in a Perkin-Elmer (Norwalk, Conn., USA) Autosystem XL gas chromatograph. The 100 nF filtering capacitor in the FID electrometer was replaced by an 8 nF capacitor. The signal from the detector was monitored at 200 Hz by a personal computer equipped with a data acquisition board.

EXAMPLE 3

Figure 14:
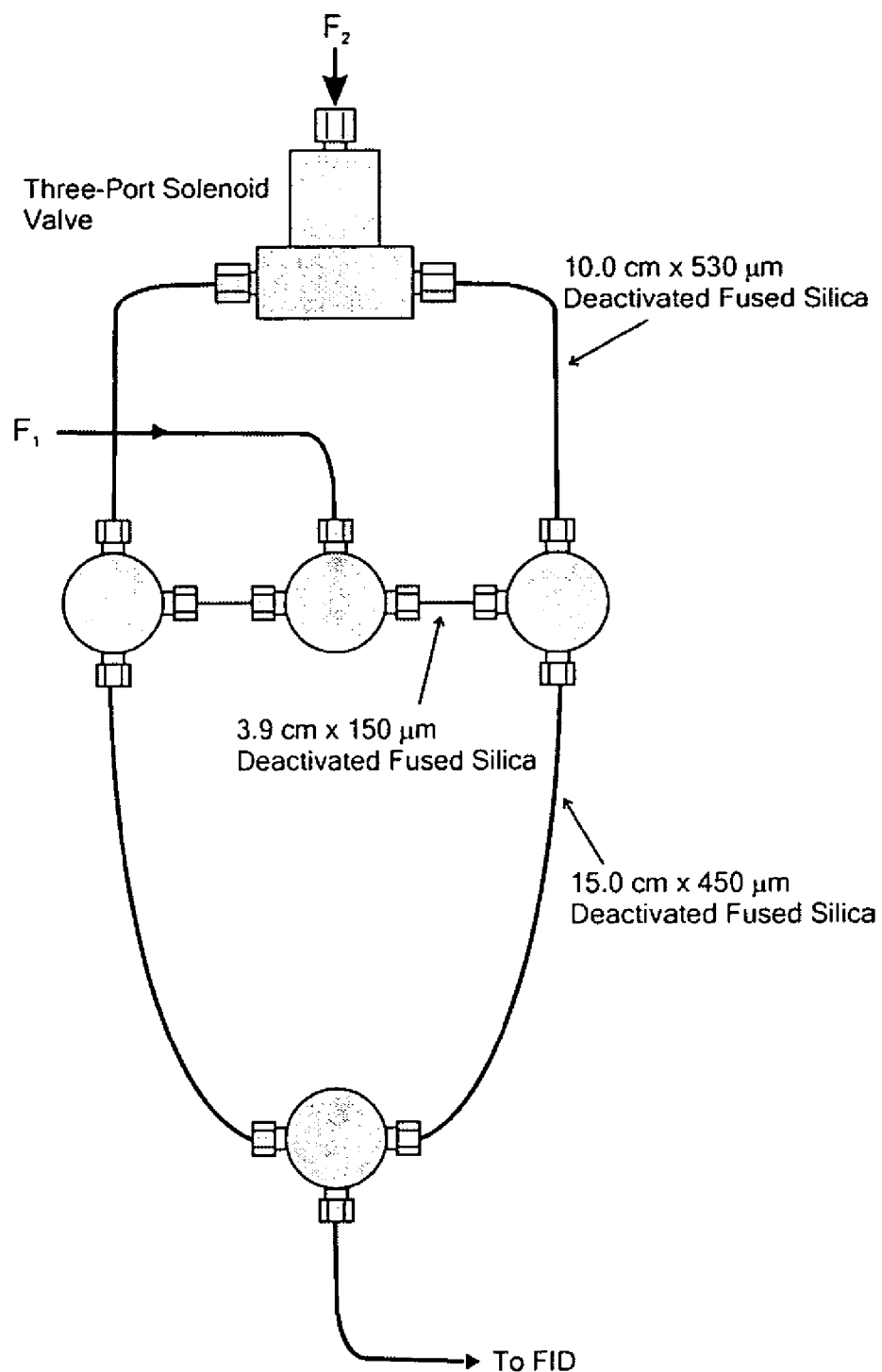
FIG. 14 is a schematic of the flow-switching device of FIG. 13.

A set of experiments was performed where the flow switching modulator sampled a series of pentane peaks. The experimental apparatus is shown in FIG. 14. A gaseous mixture of pentane in hydrogen was generated by injecting liquid pentane with a syringe pump at a rate of 0.2 µL min$^{-1}$ into a 5 mL min$^{-1}$ flow of hydrogen. This mixture was passed through a 28 µL sample loop of a multi-port diaphragm valve (VICI, Houston, Tex., USA, part number DV22-2116). The sample loop contents were injected into a 1.0 mL min$^{-1}$ primary flow of H$_2$ every 15.2 s. The pentane peaks were passed through a 500 cm×250 µm DB-1701 column (Agilent Technologies, Palo Alto, Calif., USA) before being sampled with the flow-switching device.

Peak Shapes Under Optimal Modulation Conditions

The flow-switching device was used to modulate methane with $F_1=1.0$ mL min$^{-1}$ and $F_2=20.0$ mL min$^-$. A portion of the FID signal obtained for a modulation period of 2.0 s is shown in FIG. 5. The peaks had widths at half maximum of approximately 95 ms. This is slightly lower than the theoretical minimum width of 100 ms for a 1:20 differential flow ratio with 2.0 s modulation. The peaks were characterized by an abrupt rise from the baseline followed by a plateau and then steep decent. There was a small tail that was noticeable when the peak had decreased to approximately 5% of its maximum intensity. The source of this tail is uncertain, but it is probably due to dead volume within the flow-switching device.

Figure 16:
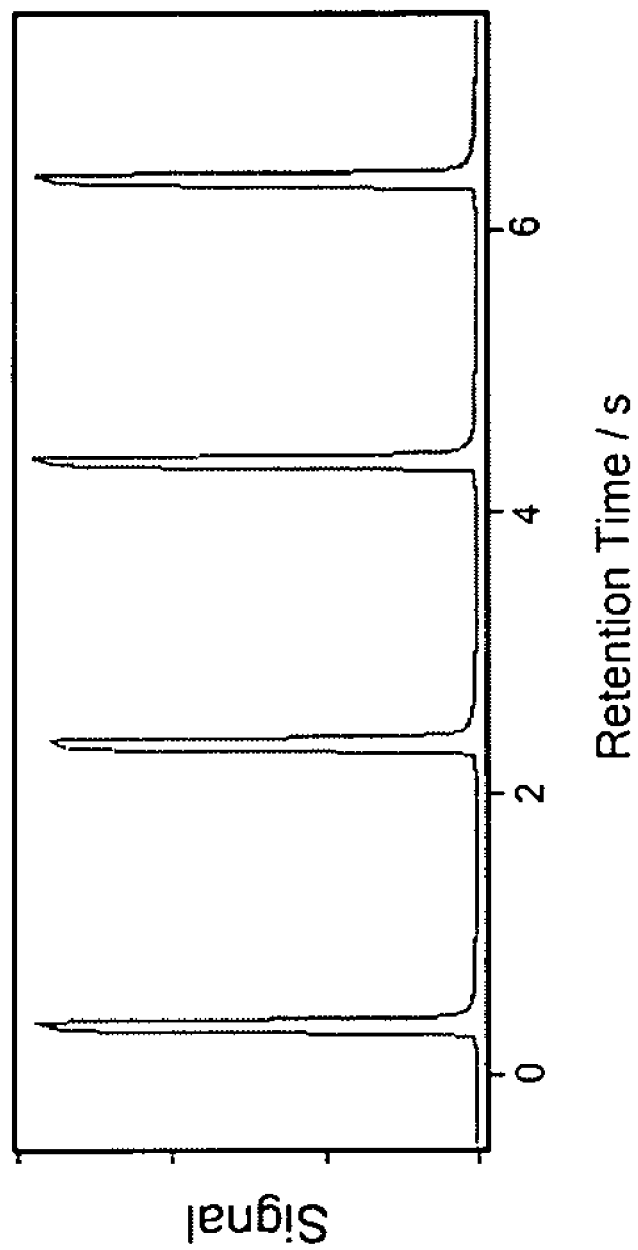
FIG. 16 is a graph showing flow switching modulation of methane under optimized conditions. Data obtained with the following experimental conditions: $F_1=1.0$ mL min$^{-1}$, $F_2=20.0$ mL min$^{-1}$, and $\tau=2.0$ s. The peaks have a width at half maximum of 95 ms.

A slight difference was observed between the shapes of the peaks injected from the left half of the device (the peaks shown in FIG. 16 near 0 and 4 s) from those injected from the right half of the device (the peaks shown in FIG. 5 near 2 and 6 s). The peaks injected from the left side of the device were approximately 3% taller and 3% narrower than those injected from the right side. This difference was presumably due to a slight asymmetry in the internal resistances of the device.

A baseline detector response of 5.5 mV was observed when methane was not injected. When methane was injected, the off-peak signal matched the baseline to within 2%. This indicates that the device properly modulates at a 1:20 flow ratio. The maximum intensity of the modulated methane peaks was approximately 500 mV (a net response of 495 mV). The detector response when methane was injected, but without modulation, was 29 mV (a net response of 23.5 mV). Thus, the modulation process increased the maximum signal by a factor of 21; very close the expected value of 20 for a 1:20 flow ratio.

The Effect of Changing the Secondary Flow

The dimensions of the flow-switching modulator were initially optimized through a trial-and-error process for $F_1$=1.0 mL min$^{-1}$ and $F_2$=20.0 mL min$^{-1}$. The effect of changing the secondary flow was examined while the primary flow was held at 1.0 mL min$^{-1}$. Several different secondary flows were tested (10.0, 12.5, 15.0, 17.5, 20.0, and 25.0 mL min$^{-1}$) Modulated peaks were observed in each case. However, the baseline was elevated when the secondary flows were less than 20.0 mL min$^{-1}$. The degree of baseline elevation increased with decreasing secondary flow. Proper modulation was observed with secondary flows of 20.0 mL min$^{-1}$ and 25.0 mL min$^{-1}$. As demonstrated in the previous section, a secondary flow of 20.0 mL min$^{-1}$ produced peaks with widths near the theoretical limit. However, a secondary flow of 25.0 mL min$^{-1}$ produced peaks that were consistently 5% wider than the theoretical limit. This broadening is most likely due to the increased cross flow (i.e., $F_2'$) caused by a higher secondary flow.

The results show that the dimensions of the capillaries used in the switching device produce optimal modulation at a 1:20 flow ratio. Although these sizes were determined empirically, a simple theoretical analysis also predicts that these dimensions are appropriate. A flow resistance model was previously used (Bueno, P. A. B., et al., J. Chromatogr. 1027, 3-10 (A 2004)) to estimate the fraction of the secondary flow that pushes the primary effluate into the collection loop($F_2'/F_2$):

$$\frac{F_2'}{F_2} = \frac{1}{2}\left[\frac{R_{BC}}{R_{BA}+R_{BC}} - \frac{F_1}{F_2}\right] \quad (3)$$

where $R_{BA}$ is the flow resistance between the union A and union B and $R_{BC}$ is the flow resistance between union B and union C. Optimal modulation is generated when the ratio $F_2'/F_2$ is near zero but positive. Thus, $R_{BC}/(R_{BA}+R_{BC})$ should be just slightly greater than $F_1/F_2$. Equivalently, this corresponds to the case when $R_{BA}/R_{BC}$ is slightly less than $(F_2/F_1)-1$. Thus, when $F_2/F_1$=20, optimal modulation should occur when $R_{BA}/R_{BC}$ is slightly less than 19. The resistance ratio of the flow-switching device can be estimated by examining the resistances of the capillary connectors. The Hagen-Poiseuille law (Giddings, J. C. *Unified Separation Science,* Wiley, New York (1991)) predicts that the laminar flow resistance of tubing is given by $$R = \frac{128\eta L}{\pi d^4} \quad (4)$$

where $\eta$ is viscosity, L is the tubing length, and d is the internal diameter of the tubing. Thus, the $R_{BA}/R_{BC}$ ratio can be estimated with the following equation:

$$\frac{R_{BA}}{R_{BC}} = \frac{L_{BA}}{L_{BC}}\frac{d_{BC}^4}{d_{BA}^4} \quad (5)$$

where $L_{BA}$ and $d_{BA}$ are the length and diameter, respectively, of the tubing connecting union A to union B and $L_{BC}$ and $d_{BC}$ are the length and diameter, respectively, of the tubing connecting union B to union C. When the dimensions of the flow-switching device are substituted into Equation 5, the resistance ratio is predicted to be 21. This theoretical value is slightly greater than the value of 19 predicted from the performance of the switching device. However, this small discrepancy is probably due to the fact that the flow resistance of the unions is neglected in Equation 5. Inclusion of a term that accounts for the resistance of the unions has the largest relative affect on $R_{BC}$ and hence decreases the theoretical prediction of the $R_{BA}/R_{BC}$ resistance ratio.

The Effect of Changing Modulation Period

Figures 17A, 17B, 17C, 17D:
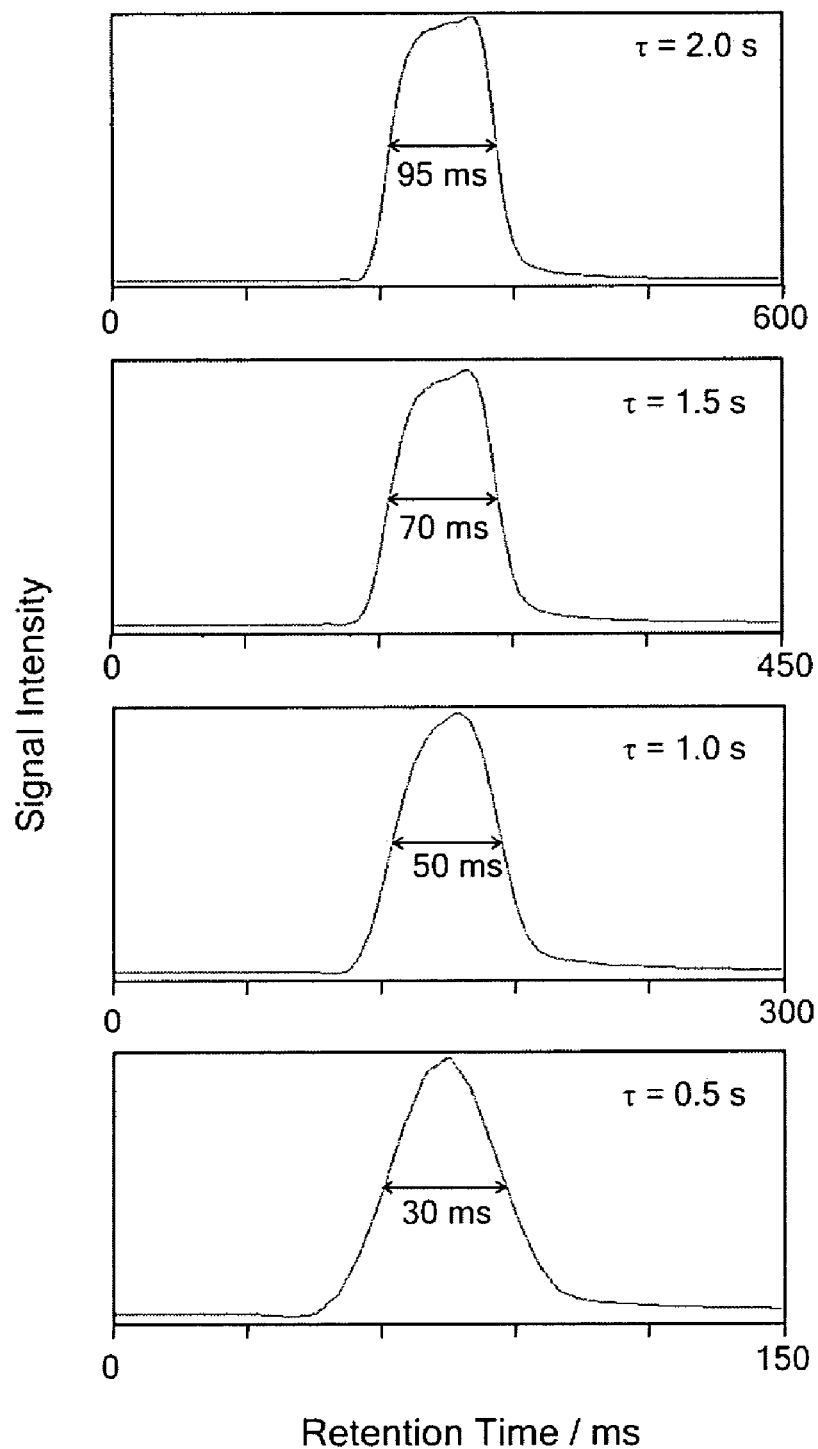
FIGS. 17A, 17B, 17C and 17D are graphs showing modulated peaks for four different modulation periods. Data obtained with $F_1=1.0$ mL min$^{-1}$ and $F_2=20.0$ mL min$^{-1}$. The absolute retention times of the peaks have been shifted to align the peaks horizontally.

The flow-switching device was tested at a 1:20 primary to secondary flow ratio with four different modulation periods: 2.0, 1.5, 1.0, and 0.5 s. FIG. 17 contains a comparison of the methane pulses produced for each modulation period. The detector response is plotted on a time scale that is 30% of the modulation period. Optimal modulation is predicted to produce peaks with widths of 100, 75, 50, and 25 ms for a modulation period of 2.0, 1.5, 1.0, and 0.5 s respectively. The observed peak widths for the 2.0, 1.5, and 1.0 s modulation periods (95, 70, and 50 ms, respectively) were slightly less or equal to the theoretical minimum width, while the peak widths for the 0.5 s modulation period were 20% greater than the optimum width. The degradation in modulator performance at short modulation periods could be due to diffusive broadening or dead volume effects. It is possible that better results for short modulation periods could be obtained by reducing the size of the flow-switching device (i.e., the modulator was designed to contain a substantially larger amount of primary column flow than necessary for a 0.5 s modulation period).

The Effect of Changing Total Flow

Figure 18A:
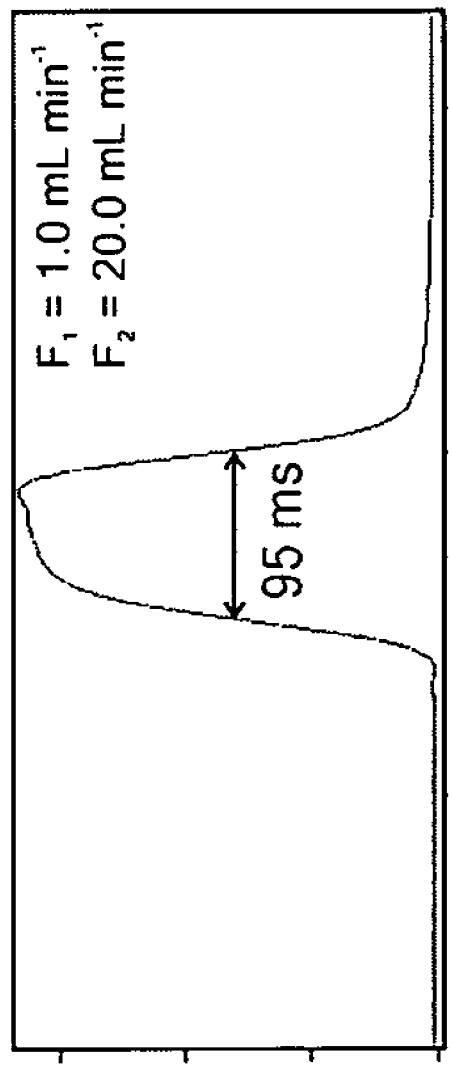
FIGS. 18A and 18B are graphs showing modulated peaks for two different values of total flow. Both peaks were obtained with a modulation period of 2.0 s. The absolute retention times of the peaks have been shifted to align the peaks horizontally.
Figure 18B:
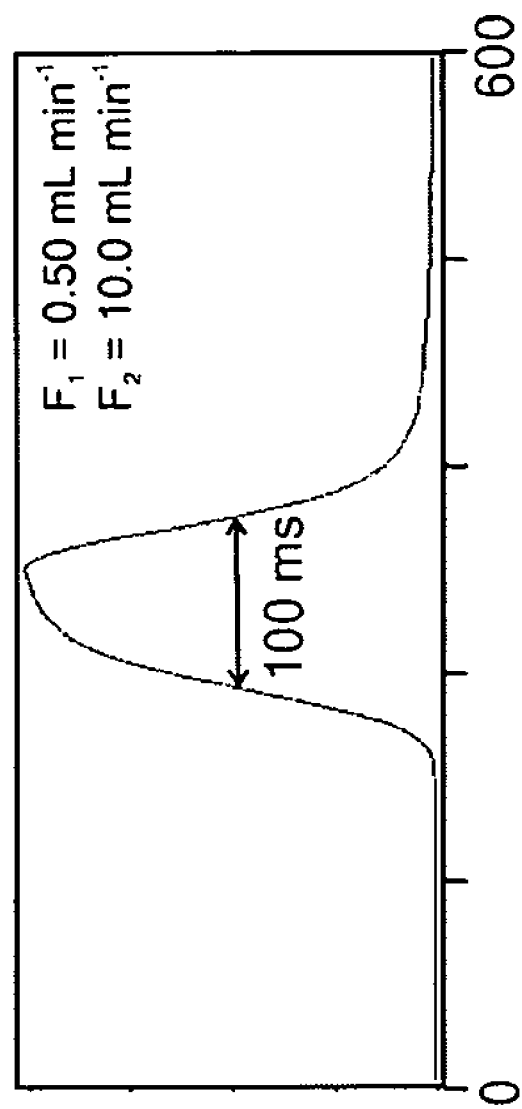
Figure 19:
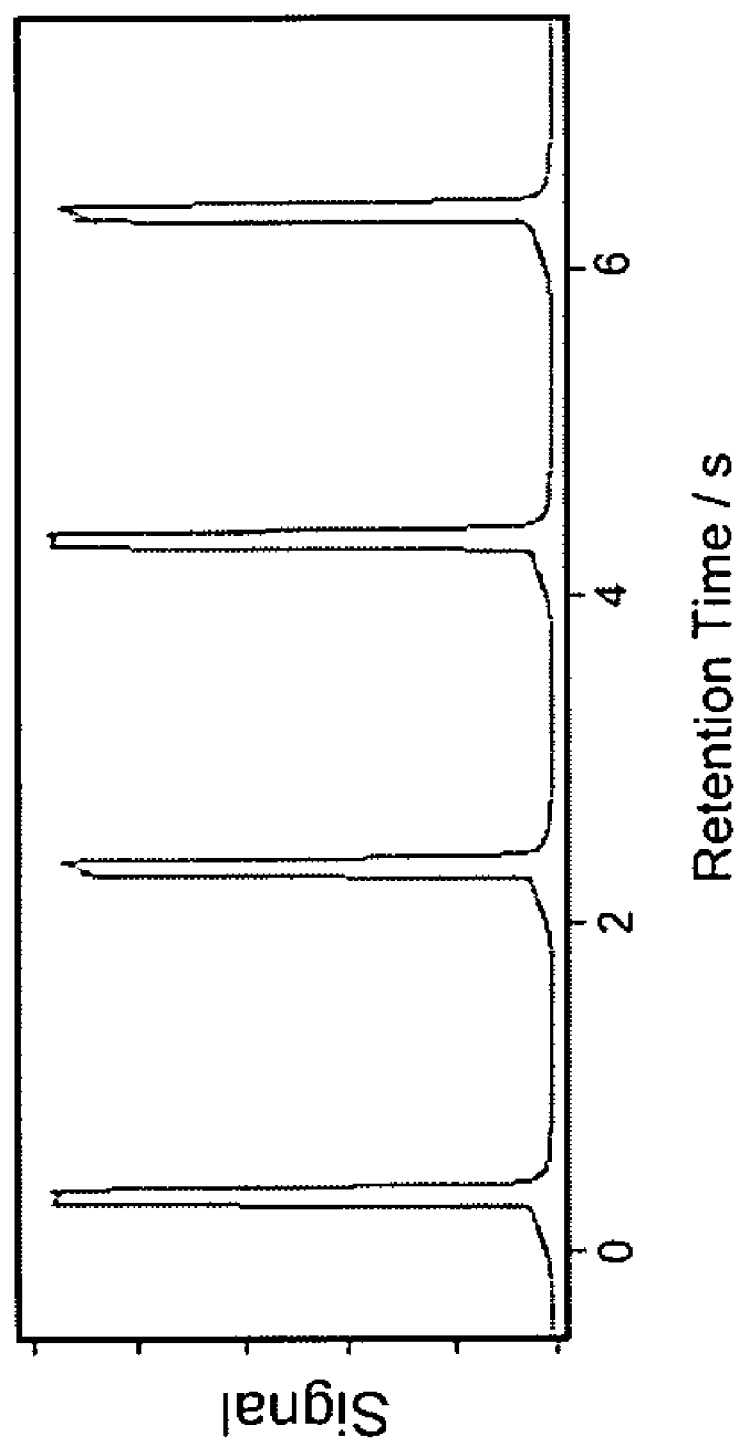
FIG. 19 is a graph showing flow switching modulation of methane. Data obtained with short capillaries (2.9 cm) connecting the central unions to the peripheral union. The following modulation conditions were employed: $F_1=1.0$ mL min$^{-1}$, $F_2=20.0$ mL min$^{-1}$, and $\tau=2.0$ s. The front shoulders of the peaks are due to overfilling of the sample loops. The peaks are 115 ms at half maximum.

In principle, proper modulation depends only on the ratio of the primary to secondary flow and not on the absolute values of the flows. A series of experiments were performed where a primary to secondary flow ratio of 1:20 was maintained, but the total flow was halved (i.e., $F_1$=0.5 mL min$^{-1}$ and $F_2$=10.0 mL min$^{-1}$). Optimal peak widths were still observed at the lower total flow. FIG. 18 shows a comparison of the peaks generated with a 2.0 s modulation period for $F_1$=0.5 mL min$^{-1}$ and $F_2$=10.0 mL min$^{-1}$ to those generated with $F_1$=1.0 mL min$^{-1}$ and $F_2$=20.0 mL min$^{-1}$. Similar results were obtained, but the lower flow peaks had slightly larger tails. Once again, reducing the size of the switching device to minimize unnecessary volume could potentially reduce this effect.

The Effect of Changing Device Dimensions

Figure 21:
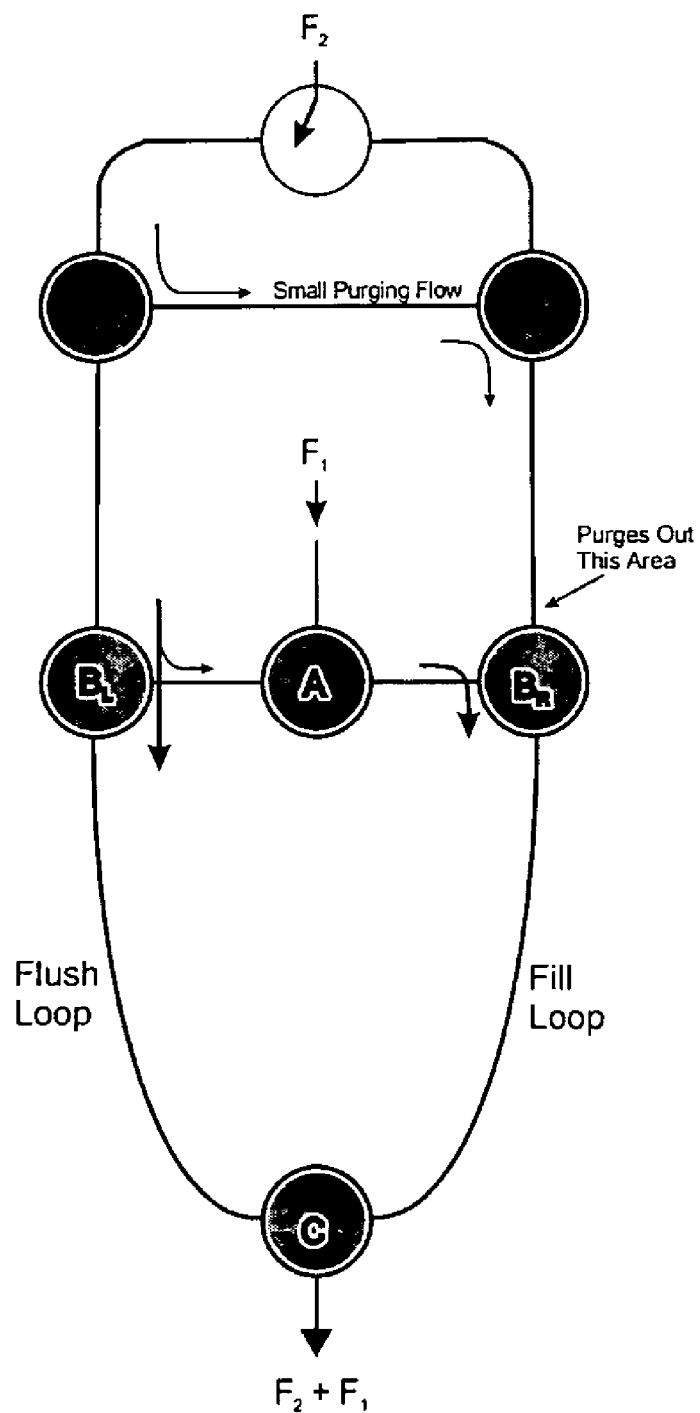
FIG. 21 shows the device of FIG. 5 with a purging flow loop after the solenoid valve 11 as shown in FIG. 7.

The effect of changing the length of the fused silica lines between the central union and the peripheral unions was examined. The lengths of these capillaries were reduced by 30% (i.e., from 3.9 to 2.7 cm). The primary flow was held at 1.0 mL min$^{-1}$. Several different secondary flows were tested (10.0, 12.5, 15.0, 17.5, 20.0, and 25.0 mL min$^{-1}$). Decreasing the connecting capillary lengths caused a decrease in the secondary flow that produced optimal performance. Properly modulated peaks, with widths within 5% of the theoretical minimum, were observed when the secondary flow was 15.0 mL min$^{-1}$. Baseline elevation was observed at secondary flows smaller than 15.0 mL min$^{-1}$. At a secondary flow of 20.0 mL min$^{-1}$, the peaks were 20% wider than the theoretical minimum. This is presumably due to a higher cross flow (i.e., $F_2'$) increasing the sample loop filling rate. For a 2.0 s modulation period and a 20 mL min$^{-1}$ secondary flow, the increased cross flow led to overfilling of the sample collection loops. As shown in FIG. 21, this effect is easily detected as a front shoulder on each injected peak. This effect was not observed for modulation periods that were 1.5 s or less.

The simple theoretical model described confirms that the flow-switching device with the shortened capillaries should produce optimal results at a primary to secondary flow ratio near 1:15. When values of $L_{BA}$=2.7 cm, $d_{BA}$=0.15 mm, $L_{BC}$=15.0 cm, and $d_{BC}$=0.45 mm are substituted into Equation 5, the value of $R_{BA}/R_{BC}$ is 1.4.6. Thus, according to Equation 3, optimal modulation is predicted at a flow ratio near 1:15.6.

Comparison to Diaphragm Valve Modulation

The performance of the flow-switching device was compared to diaphragm valve modulation. The apparatus shown in FIG. 2 was employed initially with a diaphragm valve in the place of the flow-switching device. Unfortunately, flow pulsations produced upon actuating the diaphragm valve distorted the peaks that exited the secondary column during a switching event. The peak distortion was greatly reduced by increasing the FID transfer line length from 1.6 m to 5 m. The peaks obtained with the diaphragm valve were 20% wider than the optimal peak width when a 1:20 primary to secondary flow ratio and a 2.0 s modulation period were employed. In contrast, the flow-switching device (with the 3.9 cm capillaries connecting the central union to the peripheral unions) at the same sampling conditions produced peaks that were equal to the optimal width. The peak broadening that accompanied diaphragm valve modulation is presumably due to flow pulsations.

The Modulation Of Pentane Peaks

Figure 15:
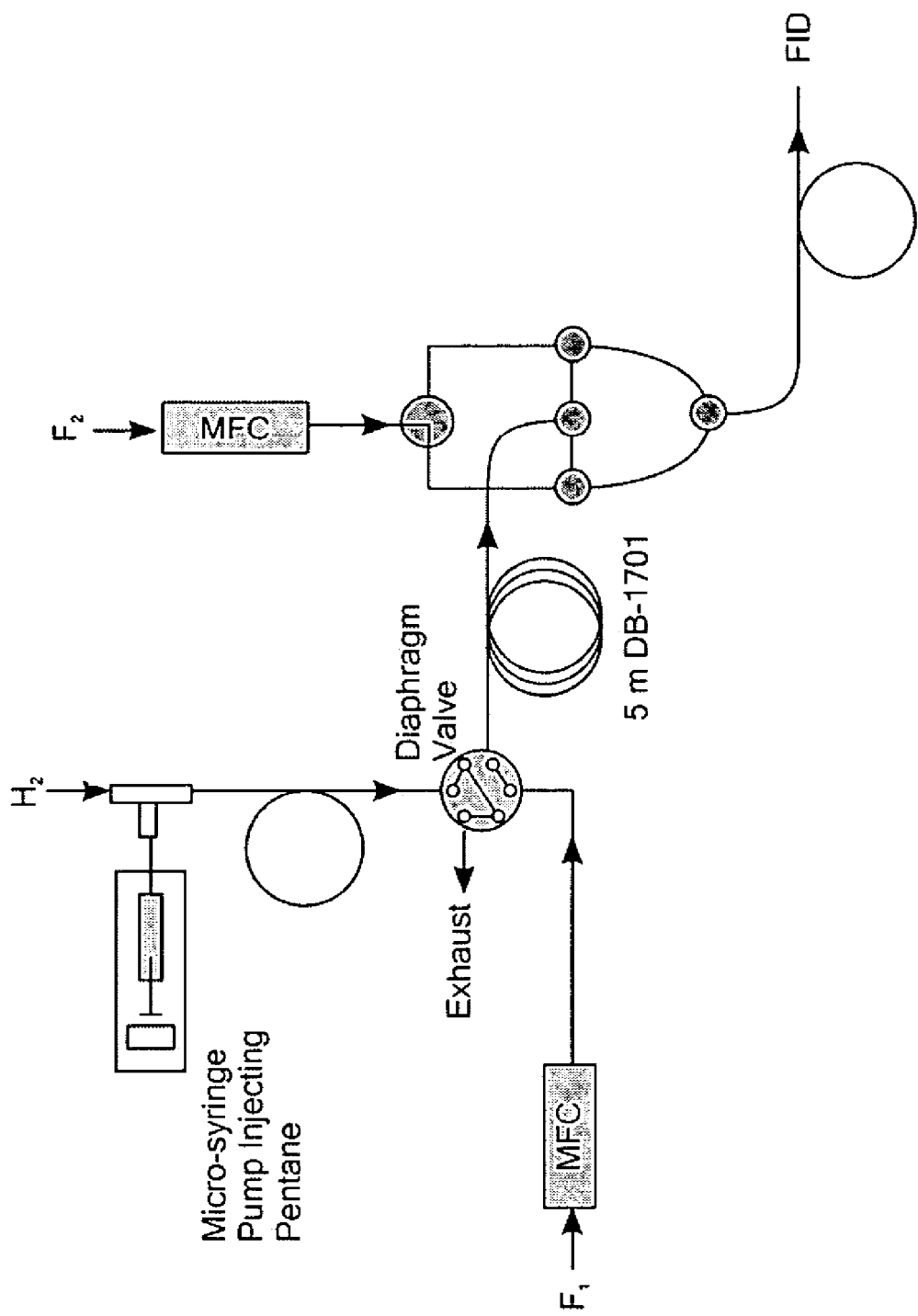
FIG. 15 is a schematic of the apparatus for the modulation of pentane peaks. A syringe pump is used to slowly add pentane to a stream of hydrogen. Small portions of the resulting mixture are injected with a diaphragm valve into the primary flow. The resulting pentane pulses are passed through a primary column and then sampled with the flow-switching device. The modulated peaks are passed through a transfer line and into a flame ionization detector (FID).
Figures 20A, 20B, 20C:
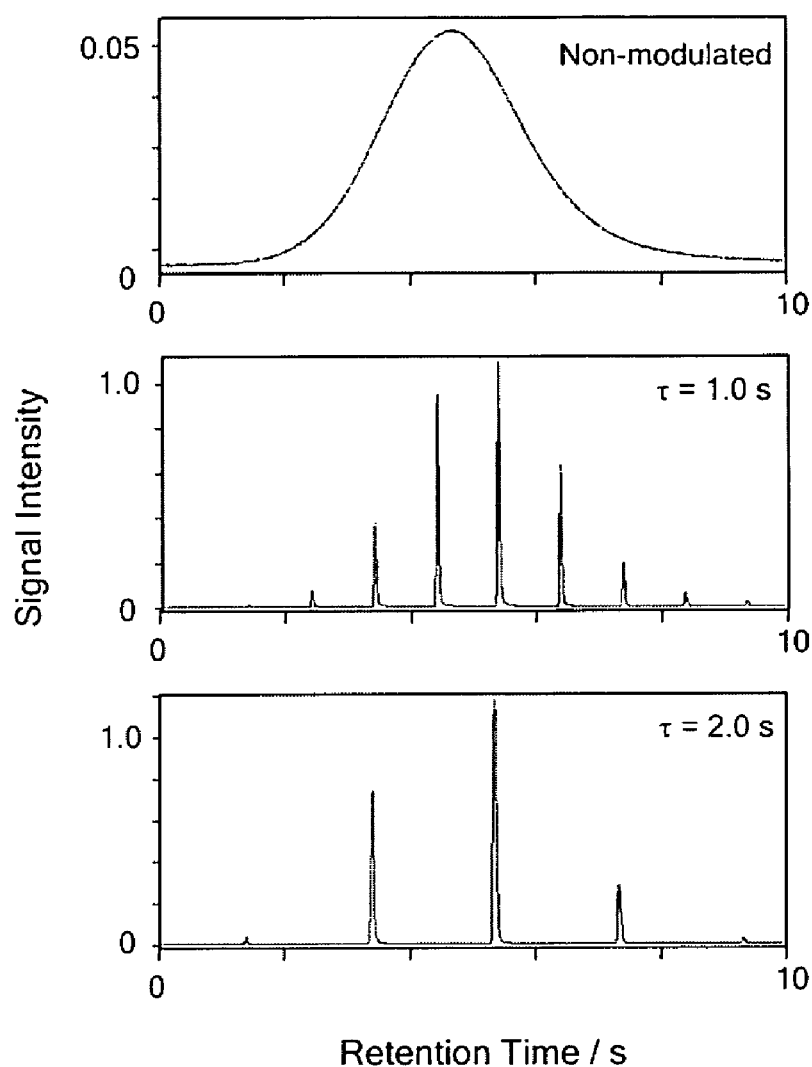
FIGS. 20A, 20B and 20C are graphs showing pentane peaks for three different modulation settings. Data obtained with $F_1=1.0$ mL min$^{-1}$ and $F_2=20.0$ ml min$^{-1}$. The absolute retention times of the peaks have been shifted to align the peaks horizontally.

The last experiment used the flow-switching modulator to sample chromatographic peaks. The apparatus (shown in FIG. 15) repeatedly injected pentane pulses into a 1.0 mL min$^{-1}$ flow of carrier gas. The modulator sampled the pentane peaks with a 20 mL min$^{-1}$ secondary flow. A typical set of results is shown in FIG. 20. When the modulator was turned off, pentane peaks with a width at half maximum of 2.80 s were observed. This corresponds to a Gaussian distribution with a 1.19 s standard deviation. When the pentane peaks were sampled with a 1.0 s modulation period, peaks were observed with a width at half maximum of 45 ms and intensity approximately 20 times greater than the non-modulated case. The value of the standard deviation along the primary retention axis was determined by integrating the manifold of peaks (Seeley, J. V., et al., Anal. Chem. 72 4346-4352 (2000); and Seeley, J. V., J. Chromatogr. A 962 21-27 (2002)). The standard deviation along the primary axis ranged from 1.23 to 1.39 s. The average standard deviation was 1.30 s. Thus, modulation with a 1.0 s period increased the peak width along the primary axis by 9%. When the pentane peaks were sampled with a 2.0 s modulation period, peaks were observed with a width at half maximum of 85 ms and intensity approximately 20 times greater than the non-modulated case. The standard deviation along the primary axis ranged from 1.36 to 1.54 s, with an average of 1.45 s. Thus, modulation with a 2.0 s period increased the peak width along the primary axis by 22%.

The degree of broadening caused by flow-switching modulation is in good agreement with theoretical predictions for the perfect modulation of a Gaussian-shaped peak. The 1.0 s modulation of a Gaussian peak with a 1.19 s standard deviation is predicted (Seeley, J. V., J. Chromatogr. 962 21-27 (A2002); and Murphy, R. E., et al., Anal. Chem. 70 1585-1594 (1998)) to produce a 2-dimensional peak with a phase-averaged standard deviation along the primary axis of 1.27 s. Modulation of the same peak with a 2.0 s period is predicted to produce a 2-dimensional peak with a phase-averaged standard deviation of 1.46 s along the primary axis. The good agreement between experiment and theory is strong evidence that the flow switching modulator does not introduce unnecessary broadening along the primary retention axis.

The results show that an inexpensive flow-switching device, constructed from readily available materials, can serve as an effective modulator. Near-optimal performance is maintained over a wide range of modulation times and total flows. In addition, the flow-switching device does not introduce extra broadening along the primary retention axis. However, high performance is only produced over a narrow range of primary to secondary flow ratios. This result has two important consequences: First, the ratio of the primary to secondary flow ratio must be maintained throughout a chromatographic run. Previous studies (Bueno, P. A. B., et al., J. Chromatogr. 1027 3-10 (A 2004)) have shown that the flow ratio is essentially constant when both the primary flow controller and the secondary flow controller are operated in constant pressure mode or in constant flow mode. Second, the dimensions of the flow switching device must be altered if the user desires to work at a substantially different primary to secondary flow ratio. Fortunately, the proper device dimensions can be predicted easily with a simple flow resistance model.

The flow switching device, unlike diaphragm valves, has no inherent temperature limitations. Thus, differential flow GC×GC separations can be performed over a wider range of temperatures. In addition, the flow switching device is capable of generating GC×GC separations without the need of additional consumables, such as liquid cryogen. This represents a distinct advantage over cryogenic modulation techniques (Kinghorn, R. M., et al., J. High Resol. Chromatogr. 21 620-622 (1998); Ledford, E. B., et al., J. High Resol. Chromatogr. 23 202-204 (2000); Beens, J., et al., J. Chromatogr. 919 127-132 (A2001); and Adahchour, M., et al., Analyst 128 213-216 (2003)): however, cryogenic modulators are capable of generating narrower peaks along the secondary retention axis and hence produce greater peak capacity.

EXAMPLE 4

Optimal performance of the flow switching device is generated when the fluid containing sample components encounters a minimal amount of stagnant regions. The presence of such regions can lead to peak tailing due to the slow transfer of sample in and out of the stagnant regions. FIG. 21 shows the location of the only region in the device that encounters sample flow and is not continually swept with carrier. This region is above the peripheral t-union that is opposite of the $F_2$ injection union. FIG. 23 shows the case when $F_2$ is injected into the left peripheral union ($B_L$), thus the stagnant region is immediately above right peripheral union ($B_R$). When $F_2$ is injected into $B_R$ (not shown in FIG. 1), then the stagnant region is above $B_R$.

There are two ways to reduce the magnitude of tailing generated by these stagnant regions. The easiest approach is to reduce the cross section of the pieces of tubing that joins the two position to the peripheral t-unions. This does not eliminate the stagnant regions, but it does reduce the amount of accessible stagnant volume and was effective. A second approach is to alter the device such that there is always at least a small flow passing through the tubing joining the two-position valve to the peripheral t-unions. The easiest way to do this is to join the two pieces of tubing with a small section of tubing that has high flow resistance (as shown in FIG. 21). This narrow-bore piece of tubing allows a small amount of purging flow (much less than $F_2$) to sweep out the tubing opposite of the main injection point. FIG. 21 shows the case when this purging flow sweeps out the region above $B_R$. When the two-position valve is switched such that the bulk of $F_2$ is injected into $B_R$, the purging flow changes directions and sweeps out the region above $B_L$.

The flow resistances must be precisely balanced in the device. This means that the capillary tubing and unions must have precise internal dimensions, that the capillary tubing can be cut to precise lengths, that the tubing can be cut cleanly with minimal blockages or burrs, and that the tubing can be connected to the unions without leaks. It was found that the combination of low-dead volume unions and deactivated fused silica tubing allowed prototypes of the device to be constructed easily.

The internal surfaces of the tubing that come in contact with the sample flow must be deactivated. If they are not, it was found that polar compounds, such as alcohols, are partially retained. This leads to tailing in the 2-D chromatogram. It was found that capillaries made of deactivated fused silica produced minimal tailing, whereas stainless steel capillary tubes produced appreciable tailing. It is possible that tubing constructed from a less active metal, such as nickel, would produce results similar to deactivated fused silica while still possessing the rugged nature of stainless steel. In any event, the tubing can be lined with fused silica.

The ratio of flow rate of the carrier fluid to fluid material is preferably between 30 to 1 and 10 to 1. The device allows fluidic switching at a rate of less than 5 Hz. The rate can be as low as 0.2 Hz. The device of the present invention is useful for combining any fluid streams where the goal is to have a pulsed output of the low flow stream from the device.

It is intended that the foregoing description be only illustrative of the present invention and that the present invention be limited only by the hereinafter appended claims.

I claim:

1. A fluidic switching device for use with a chromatographic separation column for separation of components of a sample fluid $F_1$ which comprises:

(a) a valve comprising a single inlet adapted for receiving a carrier fluid $F_2$ and with two outlets, wherein the valve is actuated by an actuator for cycling between each of the outlets during the separation;

(b) first and second tubular conduits leading from the valve to each of two separate inlets into a common first union with an outlet for $F_1$ and $F_2$ between the separate inlets;

(c) third and fourth tubular conduits as a connection between the first and second tubular conduits; and (d) a second union between the third and fourth tubular conduits adapted for flow between arms of the second union and adapted so that the sample fluid $F_1$ can be introduced and flow into the arms from a leg of the second union, wherein the device is constructed so that fluid flow is greater in the first and second conduits than in the third and fourth conduits such that when the carrier fluid $F_2$ flow is alternately switched in the valve to the one of the first or second conduits, the sample fluid $F_1$ introduced in the second union is temporarily accumulated as $F_1$ and $F_2$ in an opposite conduit of the first or second conduits from the third conduit or the fourth conduit, which accumulated fluid is subsequently flushed from the opposite of the first or second conduit by the carrier fluid $F_2$ which flows in the opposite first or second conduit upon switching of the valve from one of the outlets from the valve to the other outlet from the valve so that fluid flow from the common union is alternately carrier fluid $F_2$ or carrier fluid $F_2$ plus sample fluid $F_1$.

2. A fluid switching device for a chromatographic separation column for detecting a sample fluid $F_1$ which comprises:

a two position valve with four ports wherein the valve switches between two separate tubular conduits outside of the valve which are connected to a common union provided for flow of the carrier fluid and sample fluid alternately into the chromatographic column, wherein between a first two of the ports, a carrier fluid $F_2$ can be injected into one of the two separate conduits outside the valve and wherein simultaneously a sample fluid $F_1$ is injected between a second two of the ports to the other of the two of the tubular conduits and wherein $F_1$ and $F_2$ are alternately switched between the first two of the ports and the second two of the ports during the chromatographic separation by the column.

3. A fluidic switching device for use with a chromatographic separation column for separation of components of a sample fluid $F_1$ which comprises:

(a) a valve comprising a single inlet adapted for receiving a carrier fluid $F_2$ and two outlets wherein the valve is actuated by an actuator for cycling between each of the outlets;

(b) first and second tubular conduits of equal internal flow resistance leading from the valve to each of two separate inlets into a common first union with an outlet for $F_1$ and $F_2$ between the separate inlets;

(c) third and fourth tubular conduits of equal internal flow resistance as a connection between the first and second tubular conduits; and (d) a second union between the third and fourth tubular conduits adapted for flow between arms of the second union and adapted so that the sample fluid $F_1$ can be introduced and flow into the arms from a leg of the second union, wherein the device is constructed so that fluid flow is greater in the first and second conduits than in the third and fourth conduits such that when the carrier fluid $F_2$ flow is alternately switched in the valve to the one of the first or second conduits, the sample fluid $F_1$ introduced in the second union is temporarily accumulated as $F_1$ and $F_2$ in an opposite of the first or second conduit from the third conduit or the fourth conduit, which accumulated fluid is subsequently flushed from the opposite first or second conduit by the carrier fluid $F_2$ which flows in the opposite first or second conduit upon switching of the valve from one of the outlets from the valve to the other outlet from the valve so that the fluid flow from the common union is alternately carrier fluid $F_2$ or carrier fluid $F_2$ plus sample fluid $F_1$.

4. A chromatographic separator apparatus which comprises:
   (a) a fluidic switching device as in claim 1 or 2; and
   (b) at least one chromatographic column connected to the leg of the first union; wherein the device is adapted to move units of the sample fluid $F_1$ mixed with the carrier fluid $F_2$ into the column between units of the carrier fluid alone.

5. The apparatus of claim 4 wherein the device is mounted inside an oven with the valve on an outside of the oven and insulated from the inside of the oven.

6. The device of any one of claims 1, 3, 4 or 5 wherein the conduits comprise fused silica tubing over which the fluid flows.

7. The device of any one of claims 1, 3, 4 or 5 wherein the valves, conduits and unions are adapted for a gas as the fluid.

8. A method for fluidic switching which comprises:
   (a) providing a fluidic switching device as in claim 1; and
   (b) introducing the carrier fluid $F_2$ into the inlet of the valve and the sample fluid $F_1$ into the inlet into the second union wherein the valve delivers units of the sample fluid $F_1$ mixed with the carrier fluid between units of the carrier fluid alone to the outlet of the first union.

9. The method of claim 8 wherein the outlet of the first union is connected to at least one chromatographic column.

10. The method of claim 8 or 9 wherein the fluidic device except for the valve is heated inside an oven.

11. The method of claim 8 or 9 wherein the fluid material and carrier fluid are a gas.

12. The method of claim 8 or 9 wherein the first and second conduits and separately the third and fourth conduits have identical cross-sections along their length.

13. The method of claim 8 or 9 wherein the ratio of fluid flow rate of the carrier fluid $F_2$ to sample fluid $F_1$ is between about 30 to 1 and 10 to 1.

14. The device of claim 1 with a purging flow line between the first and second tubular conduits before the first common union.

15. The device of claim 3 with a purging flow line between the first and second tubular conduits before the first common union.

* * * * *

UNITED STATES PATENT AND TRADEMARK OFFICE
CERTIFICATE OF CORRECTION

PATENT NO. : 7,247,189 B2
APPLICATION NO. : 10/840767
DATED : July 24, 2007
INVENTOR(S) : John V. Seeley Page 1 of 1

It is certified that error appears in the above-identified patent and that said Letters Patent is hereby corrected as shown below:

Column 14, line 59, "20.0 mL min" should be --20.0 mL min$^{-1}$--.

Column 17, line 32, "1.4.6" should be --14.6--.

Signed and Sealed this

Fourth Day of December, 2007

JON W. DUDAS
*Director of the United States Patent and Trademark Office*